US012734481B2

(12) United States Patent
Ping et al.

(10) Patent No.: US 12,734,481 B2
(45) Date of Patent: Sep. 15, 2026

(54) MATERIALS INCLUDING ALKYL DIAMINE-SUBSTITUTED ARYL COMPOUNDS, METHODS OF MAKING, AND METHODS OF SEPARATING $CO_2$

(71) Applicants: Georgia Tech Research Corporation, Atlanta, GA (US); Global Thermostat Operations, LLC, Brighton, CO (US)

(72) Inventors: Eric W. Ping, Thornton, CO (US); Miles A. Sakwa-Novak, Arvada, CO (US); Christopher W. Jones, Atlanta, GA (US); Dharam Raj Kumar, Atlanta, GA (US); Cornelia Rosu, Bear, DE (US)

(73) Assignees: Georgia Tech Research Corporation, Atlanta, GA (US); Global Thermostat Operations, LLC, Brighton, CO (US)

( * ) Notice: Subject to any disclaimer, the term of this patent is extended or adjusted under 35 U.S.C. 154(b) by 1156 days.

(21) Appl. No.: 17/453,680

(22) Filed: Nov. 5, 2021

(65) Prior Publication Data

US 2022/0096999 A1 Mar. 31, 2022

Related U.S. Application Data

(63) Continuation-in-part of application No. 17/338,064, filed on Jun. 3, 2021, now abandoned, and a continuation-in-part of application No. 17/338,060, filed on Jun. 3, 2021, now abandoned.

(60) Provisional application No. 63/034,001, filed on Jun. 3, 2020, provisional application No. 63/034,243, filed on Jun. 3, 2020.

(51) Int. Cl.

| | |
|---|---|
| ***B01D 53/62*** | (2006.01) |
| ***B01D 53/81*** | (2006.01) |
| ***B01D 53/96*** | (2006.01) |
| ***B01J 20/10*** | (2006.01) |
| ***B01J 20/32*** | (2006.01) |
| ***C07C 211/53*** | (2006.01) |

(52) U.S. Cl.

CPC ............ *B01D 53/62* (2013.01); *B01D 53/81* (2013.01); *B01D 53/96* (2013.01); *B01J 20/103* (2013.01); *B01J 20/3204* (2013.01); *B01J 20/3255* (2013.01); *C07C 211/53* (2013.01); *B01D 2253/20* (2013.01); *B01D 2257/504* (2013.01); *B01D 2258/0283* (2013.01); *B01J 2220/46* (2013.01)

(58) Field of Classification Search

CPC ........ B01D 53/62; B01D 53/81; B01D 53/96; B01D 2253/20; B01D 2257/504; B01D 2258/0283; B01J 20/103; B01J 20/3204; B01J 20/3255; B01J 2220/46; C07C 211/53

See application file for complete search history.

(56) References Cited

U.S. PATENT DOCUMENTS

| | | | |
|---|---|---|---|
| 8,491,705 B2 | 7/2013 | Choi et al. | |
| 2015/0038512 A1 | 2/2015 | Looper et al. | |
| 2015/0038705 A1* | 2/2015 | Williams | C07C 211/27 564/337 |
| 2015/0182903 A1* | 7/2015 | Zhou | B01J 20/267 521/154 |
| 2021/0260561 A1 | 8/2021 | Onaizi et al. | |
| 2022/0096991 A1 | 3/2022 | Jones et al. | |
| 2022/0169593 A1* | 6/2022 | Jones | C07C 209/06 |

OTHER PUBLICATIONS

T. Ghanbari et al., 707 Science of the Total Environment (2020) (Year: 2020).*
IUPAC, Compendium of Chemical Terminology, Gold Book, pp. 60, 73, 108-110, 114 (2014) (Year: 2014).*
D. Kumar et al., ACS Sustainable Chemistry & Engineering, 10971-10982 (2020) (Year: 2020).*
W. Li et al., 3 ChemSusChem, 899-903 (2010) (Year: 2010).*
D. Zhou et al., 9 ChemCatChem, 4598-4606 (2017) (Year: 2017).*
D. Zhou et al., 57 Inorganic Chemistry, 2695-2704 (2018) (Year: 2018).*
W. Lu et al., 51 Angew. Chem. Int. Ed., 7480-7484 (2012) (Year: 2012).*
D. Markl et al, 538 International Journal of Pharmaceutics, 188-214 (2018) (Year: 2018).*

* cited by examiner

*Primary Examiner* — Alexander R Pagano
(74) *Attorney, Agent, or Firm* — Wolf, Greenfield & Sacks, P.C.

(57) ABSTRACT

The present disclosure provides for materials comprising porous structures supporting (e.g., disposed therein and/or thereon) alkyl diamine-substituted aryl compounds, methods of making the materials and components thereof, methods of use thereof, and the like. In an aspect, the materials can be used to separate $CO_2$ and/or adsorb $CO_2$ in one or more $CO_2$ capture or separation applications. In one aspect, the sorbent material can be used to separate and capture $CO_2$ in gas mixtures (e.g., ambient air, flue gas, exhaust, and mixtures of these) in a wide range of concentrations. As a result, embodiments of the present disclosure are advantageous in that they can be used in different types of $CO_2$ concentration environments.

12 Claims, 14 Drawing Sheets

MATERIALS INCLUDING ALKYL DIAMINE-SUBSTITUTED ARYL COMPOUNDS, METHODS OF MAKING, AND METHODS OF SEPARATING $CO_2$

CLAIM OF PRIORITY TO RELATED APPLICATION

This application is a Continuation in Part of U.S. Ser. No. 17/338,060 filed on Jun. 3, 2021, which claims the benefit under 35 U.S.C. § 119(e) of U.S. Provisional Application Ser. No. 63/034,001, filed on Jun. 3, 2020, and is a Continuation in Part of U.S. Ser. No. 17/338,064, filed on Jun. 3, 2021, which claims the benefit under 35 U.S.C. § 119(e) of U.S. Provisional Application Ser. No. 63/034,243 filed on Jun. 3, 2020, each of which is entirely incorporated herein by reference in their entirety.

In addition, this application is a Continuation in Part application and claims priority to co-pending U.S. Utility application entitled "Composite Materials Containing Alkyl-Aryl Amine Rich Molecules and Mesoporous Supports for Direct Air $CO_2$ Capture" having Ser. No. 17/338,064, filed on Jun. 3, 2021, and where this application (Ser. No. 17/338,064) claims priority to U.S. provisional application entitled "Composite Materials Containing Alkyl-Aryl Amine Rich Molecules and Mesoporous Supports for Direct Air $CO_2$ Capture" having Ser. No. 63/034,243, filed on Jun. 3, 2020; each of which is entirely incorporated herein by reference.

BACKGROUND

The increase in atmospheric $CO_2$ concentration has alarming implications for global climate change. Intense efforts have been dedicated by researchers to develop effective technologies for carbon capture and sequestration (CCS), with an approach recently recognized as potentially critical to rapid climate stabilization, the direct removal of $CO_2$ from the atmosphere, or direct air capture. Direct air capture of $CO_2$ (DAC) from the atmosphere has been recently developed as a potential negative emissions technology (NET) due to its technological, scalability and environmental advantages. There is a need to develop technologies to address these problems.

SUMMARY

The present disclosure provides for materials comprising porous structures supporting (e.g., disposed therein and/or thereon) alkyl diamine-substituted aryl compounds, methods of making the materials and components thereof, methods of use thereof, and the like. In an aspect, the materials can be used to separate $CO_2$ and/or adsorb $CO_2$ in one or more $CO_2$ capture or separation applications. In an aspect, the present disclosure provides for materials comprising a porous structure comprising an alkyl diamine-substituted aryl compound supported by the porous structure. In one aspect, the organic loading of the alkyl diamine-substituted aryl compound on the porous structure is about 10% to 80% based on thermogravimetric analysis. In another aspect, the alkyl diamine-substituted aryl compound is physically impregnated in the porous structure (and optionally not covalently bonded to the surface of the pores). And while in yet another aspect, the alkyl diamine-substituted aryl compound is covalently bonded to the porous structure. In an aspect, the alkyl diamine-substituted aryl compound can be deposited on the surface of the porous structure, confined within the pore volume of the porous structure; or a combination thereof.

In an aspect, the alkyl of the alkyl diamine-substituted aryl compound can be an ethyl group, propyl group or butyl group. The alkyl diamine-substituted aryl compound can include 3 to 6 alkyl diamine moieties, in particular, 3 or 6 alkyl diamine moieties. For example, the alkyl diamine-substituted aryl compound can include 3 alkyl diamine moieties, optionally in the 1, 3, and 5 positions on the alkyl diamine-substituted aryl compound.

In an aspect, the porous structure can be selected from the group consisting of silica, alumina, aluminosilicates, zirconia, germania, magnesia, titania, hafnia, mixed oxides composed of those elements, a combination thereof; or the porous structure can be selected from the group consisting of a porous metal organic framework, a porous polymer structure, and a porous carbon structure.

In an aspect, the present disclosure provides for methods of separating $CO_2$ from a gas mixture, comprising: exposing a gas mixture to a porous structure having supported therein an alkyl diamine-substituted aryl compound; capturing the $CO_2$ in the porous structure; and releasing the $CO_2$ from the porous structure. In an aspect, the gas mixture can include ambient air or a mixture of ambient air and flue gas.

Other structures, methods, structures, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of this disclosure. Moreover, in the drawings, like reference numerals designate corresponding parts throughout the several views.

(FIG. 5B) 110° C. followed by 12 h exposure to 400 ppm $CO_2$ at 35° C.

DETAILED DESCRIPTION

Figures 1A, 1B, 1C, 1D:
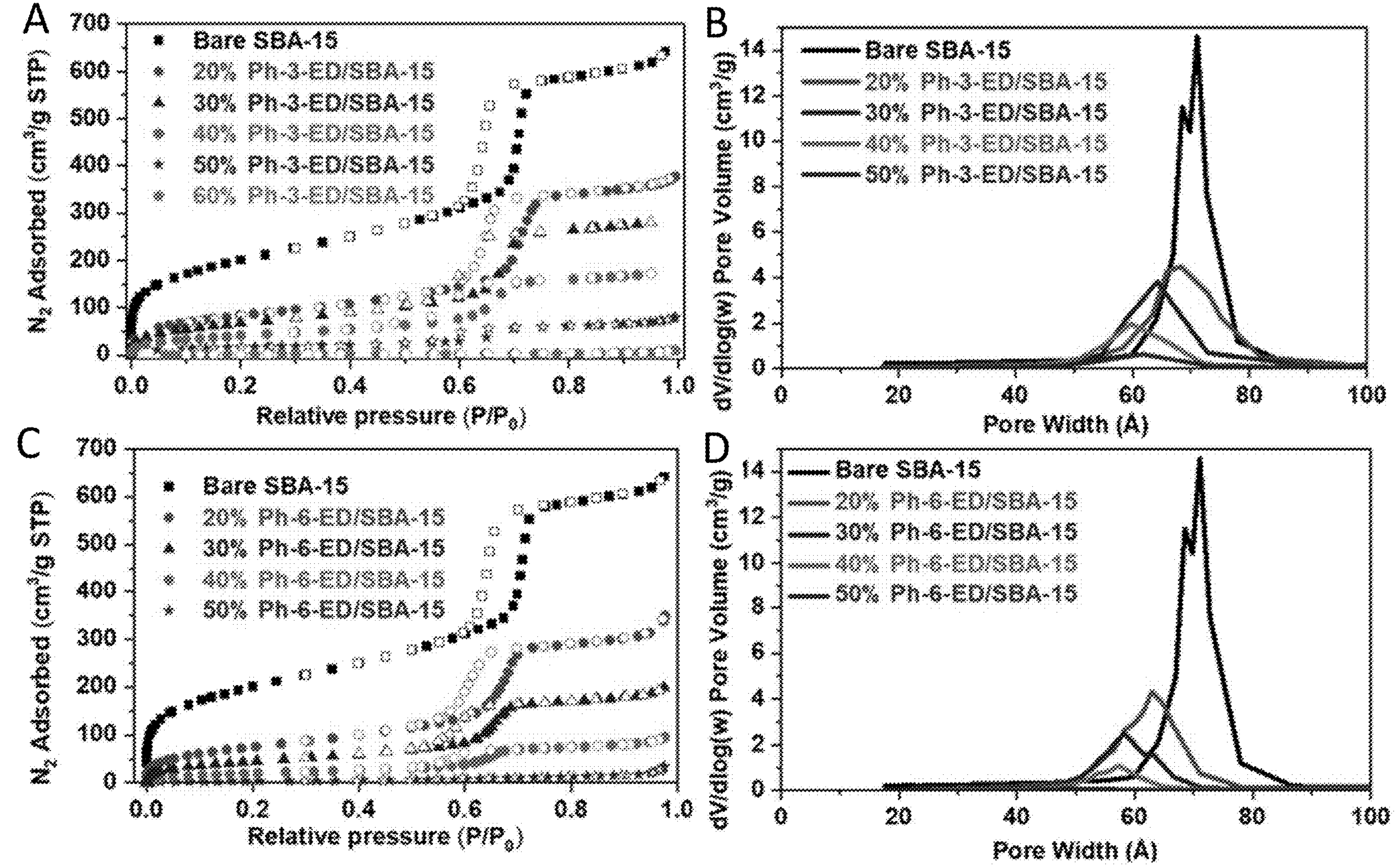
FIGS. 1A-ID illustrate nitrogen physisorption isotherms (FIG. 1A and FIG. 1C) and pore size distribution (FIG. 1B and FIG. 1D) for Ph-3-ED/SBA-15 and Ph-6-ED/SBA-15 composites of various organic loadings (0%-60%) recorded at 77K.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic chemistry, inorganic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary.

It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

The term "alkyl" refers to straight or branched chain hydrocarbon groups having 1 to 20 carbon atoms such as methyl, ethyl, n-propyl, i-propyl, n-butyl, i-butyl, t-butyl, pentyl, hexyl, heptyl, octyl, and the like. In a particular aspect, the term "alkyl" refers to ethyl, n-propyl, i-propyl, n-butyl, i-butyl, and t-butyl. The alkyl group can be substituted (e.g., a halogen).

The term "diamine" refers to an amine moiety that includes two amino groups. For example, diamine used in conjunction with alkyl diamine can include ethylenediamine moiety and propylenediamine moiety.

DISCUSSION

The present disclosure provides for materials comprising porous structures supporting (e.g., disposed therein and/or thereon the surfaces of the pores) alkyl diamine-substituted aryl compounds, methods of making the materials and components thereof, methods of use thereof, and the like. In an aspect, the materials can be referred to as "sorbent materials" and can be used to separate $CO_2$ and/or adsorb $CO_2$ in one or more $CO_2$ capture or separation applications. In one aspect, the sorbent material can be used to separate and capture $CO_2$ in gas mixtures (e.g., ambient air, flue gas, exhaust, and mixtures of these) in a wide range of concentrations such as from about 100 ppm to 20% of $CO_2$ in a gas mixture (e.g., low (e.g., about 50 to 1000 ppm $CO_2$ in a gas mixture), medium (e.g., 0.1 to 1% $CO_2$ in a gas mixture) and high concentrations (e.g., 1 to 20% $CO_2$ in a gas mixture)). As a result, embodiments of the present disclosure are advantageous in that they can be used in different types of $CO_2$ concentration environments. In addition, relative to other $CO_2$ sorbents, embodiments of the present disclosure show equivalent or superior absorption characteristics, while exhibiting excellent stability to oxidative degradation.

In an embodiment, the sorbent material can be used to separate $CO_2$ from gas mixtures by adsorbing $CO_2$ and then controllably releasing the $CO_2$. In this regard, embodiments of the present disclosure can be used to separate and remove (e.g., capture) $CO_2$ from a gas mixture produced by the use (e.g., burning) of fossil fuels (e.g., flue gas) from $CO_2$ in the ambient air or mixtures of these. The sorbent material can be regenerated for regenerative adsorption processes. In this regard, the sorbent material has the ability to adsorb and desorb $CO_2$ repeatedly by temperature swing, pressure swing, steam swing, concentration swing, combinations thereof, or other dynamic processes. In an embodiment, the steam swing process can include exposing the sorbent material to steam, where the temperature of the steam is about 60° C. to 150° C. and the pressure of the steam is about 0.2 bara to 5 bara.

As described generally, the present disclosure provides for a material sorbent that includes a porous structure that has an alkyl diamine-substituted aryl compound supported by the porous structure ("porous structure" can include a structure having pores in its surface or a structure having a porous layer or coating on the surface of the structure (where the structure itself may or may not be porous)). In an aspect, the alkyl diamine-substituted aryl compound is physically impregnated in a plurality of pores (internal pore volume of the pores of the porous structure) of the porous structure and optionally not covalently bonded to the porous structure. In regard to the alkyl diamine-substituted aryl compounds being physically impregnated in the pores of the porous structure and not covalently bonded to the internal surface of the pores of the porous structure, the alkyl diamine-substituted aryl compounds can otherwise be bonded or attached to the surface (e.g., Van der Waals, ionic bonds or hydrogen bonds).

In another aspect, the alkyl diamine-substituted aryl compound can be covalently bonded to the porous structure. In yet another aspect, there is a mixture of the alkyl diamine-substituted aryl compound that is physically impregnated in the porous structure and a portion that is covalently bonded to the porous structure. In another embodiment, the alkyl diamine-substituted aryl compounds can be covalently bonded (e.g., directly to the surface or via a linker group) to the surface of the material, which may include the internal surface of pores for a porous layer or porous structure, although the alkyl diamine-substituted aryl compounds can be otherwise bonded or attached to the surface (e.g., Van der Waals, ionic bonds or hydrogen bonds). In an aspect, the covalent bonding can be achieved using known techniques in the art. For example, the alkyl diamine-substituted aryl compounds can be physically impregnated in the internal volume pores of the porous structure and/or can be grafted (e.g., covalently bonded directly or indirectly) to the internal surface of the pores of the porous structure.

In an embodiment, the porous structure can have an organic loading of the alkyl diamine-substituted aryl compound of about 10% to 80%, about 20% to 60%, or about 40% to 60%, where the loading amount is determined using thermogravimetric analysis (TGA). A brief written description of this is given in Example 1.

In a particular aspect and discussed in more detail in Example 1, the sorbent material can have a high surface area (e.g., porous layers and/or porous structure surface) and the sorbent material enables the structure to have a high $CO_2$ sorption capacity. In an embodiment, the sorbent material includes the alkyl diamine-substituted aryl compounds within the pore volume of the pores of the porous layers and/or porous structure surface. In an aspect, the pores (e.g., mesopores) are not be overfilled by the alkyl diamine-substituted aryl compounds, so there exists suitable space for the transport of gases through the pores via diffusion, although other gas transport processes can occur (e.g., advection, convection, and the like). In another aspect, the pores (e.g., mesopores) can be substantially filled by the alkyl diamine-substituted aryl compounds and still function to adsorb $CO_2$. It is also contemplated that a system can be used where the transport of gases is through a pressure drop through the pores. In other embodiments where the pore size is sufficiently large and/or the material is a monolith, the gas can contact the alkyl diamine-substituted aryl compounds by controlling the flow of the gas relative to the orientation of the material to enhance the performance of the material. Additional details are provided herein.

In an aspect, the alkyl diamine-substituted aryl compounds can be represented by Structure A and Structure B below:

Structure A

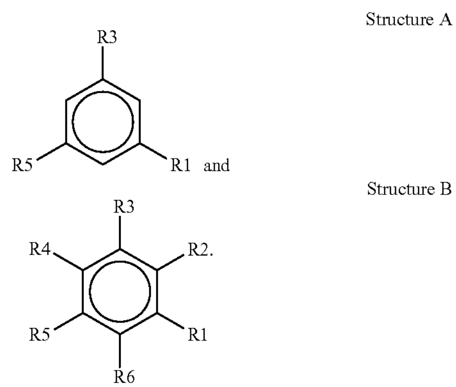

and

Structure B

Each of R1, R2, R3, R4, R5, and R6 can be independently selected from an alkyl diamine. In an aspect, the alkyl moiety of the alkyl diamine can a C2 (ethyl moiety) to C4 group (butyl moiety), a C2 or C3 (propyl moiety) group, or a C2 group. In a particular aspect, for each of R1, R3, and R5 the alkyl moiety of the alkyl diamine can be a C2 or C3 group or a C2 group. In another aspect, for each of R1, R2, R3, R4, R5, and R6 the alkyl moiety of the alkyl diamine can be a C2 or C3 group or a C2 group. As shown in Example 1, scheme 1, both Structure A or Structure B can include ethylenediamine or propylenediamine as the R1, R3, and R5 group or R1, R2, R3, R4, R5, and R6 group, respectively.

While Structure A shows the 2 position, 4 position, and 6 position of the aryl group as being H, other embodiments include the option that the 2 position, 4 position, and 6 position of the aryl group, or any combination thereof can independently have a moiety selected from H, halogen, or an alkyl (e.g., C1 to C3 alkyl moiety).

In particular and described in more detail in Example 1, TGA and DSC analyses suggest that these sorbent materials have good thermal stability. An increase in the amine loading led to an increase in $CO_2$ adsorption capacity measured under simulated dry direct air capture (DAC) conditions. The sorbent material including the 1, 3, 5 alkyl diamine-substituted aryl compounds show superior $CO_2$ adsorption capacities compared to the sorbent material including the 1, 2, 3, 4, 5, 6 alkyl diamine-substituted aryl compounds homologues, likely due to the bulkier molecular structure of the 1, 2, 3, 4, 5, 6 alkyl diamine-substituted aryl compounds. The highest $CO_2$ capacity was demonstrated with the sorbent material including the 1, 3, 5 ethylenediamine-substituted aryl compounds, 1.9 mmol/$g_{SiO2}$ and an amine efficiency of 0.13 mmol $CO_2$/mmol N at 35° C. under dry conditions. Temperature-swing adsorption/desorption cycles showed that the sorbent materials had relatively stable performance that is comparable to that of the benchmark polyethyleimine (PEI) and linear polypropyleneimine (PPI) supported SBA-15 sorbents. The sorbent material including 60% organic loading of the 1, 3, 5 ethylenediamine-substituted aryl compounds showed a two-fold increase in the $CO_2$ adsorption capacity under humid conditions (2.9 mmol/$g_{SiO2}$ @ 30%, RH) and a 70% increase in amine efficiency (0.17 mmol $CO_2$/mmol N). Thus, these aromatic-based alkyl-diamine molecules can be used as practical $CO_2$ sorbents targeting DAC technologies.

In general, the methods of making the sorbent material, the porous material and the alkyl diamine-substituted aryl compound are described in Example 1. In an aspect, the present disclosure provides for a method of making an alkyl diamine-substituted aryl compound, where the method includes mixing 1,2,3,4,5,6-hexakis(halidmethyl)benzene with alkyl-diamine and a base (e.g., KOH) under and an inert gaseous atmosphere at room temperature for about 12 to 36 hours or about 24 hours to form a 1,2,3,4,5,6-hexakis (alkyl-diamine)aryl compound. In an aspect, the halide can be bromine. The alkyl moiety can be any of those described herein.

While having described various aspects of the present disclosure, additional discussion about features and aspects is now provided. In general, the porous structure can include powders, a pellet, a foam, a laminate, an extrudate particle, a film, a sheet, a mesh, a foil, flakes, a wire, a rod, a monolith, a honeycomb structure, or combinations thereof. The porous structure can be gas permeable scaffold that gas can be flow through and/or over the surface over to separate $CO_2$ from a gas mixture. In an aspect, the porous structure can be made of a material that is hydrothermally stable.

In an embodiment, the porous structure can be made of one or more types of materials such as ceramic, metal, metal oxide, polymer-based material, cellulose, carbon, porous metal organic framework, or fiberglass. In an aspect, the ceramic structure can be selected from cordierite, alumina (e.g., γ-alumina, θ-alumina, δ-alumina), cordierite-α-alumina, silica, aluminosilicates, zirconia, germania, magnesia, titania, hafnia, silicon nitride, zircon mullite, spodumene, alumina-silica magnesia, zircon silicate, sillimanite, magnesium silicates, zircon, petalite, and combinations thereof. In an aspect, the metal or metal oxide structure can be aluminum, titanium, stainless steel, a Fe—Cr alloy, or a Cr—Al—Fe alloy. In cases where the oxide contains a formal charge, the charge can be balanced by appropriate counter-ions, such as cations of $NR_4$, Na, K, Ca, Mg, Li, H, Rb, Sr, Ba, Cs or anions including phosphate, phosphite, sulfate, sulfate, nitrate, nitrite, chloride, bromide and the like.

In an aspect, the polymer based material can be a polymer and/or copolymer of polyolefin(s), polyester(s), polyurethane(s), polycarbonate(s), polyetheretherketone(s), polyphenylene oxide(s), polyether sulfone(s), melamine(s), polyamide(s), polyacrylates, polystyrenes, polyacrylonitriles, polyimides, polyfurfural alcohol, phenol furfuryl alcohol, melamine formaldehydes, resorcinol formaldehydes, cresol formaldehyde, phenol formaldehyde, polyvinyl alcohol dialdehyde, polycyanurates, polyacrylamides, various epoxies, agar, and agarose, or combinations thereof.

In an embodiment, the porous structures can be macroporous, mesoporous, microporous, or mixtures thereof. In an aspect, a macroporous surface can include mesopores, and/or micropores, within one or more of the macropores, while a mesoporous surface can include micropores, and so on. In an aspect, the porous structure is mesoporous. In an aspect, the pores can extend through the porous structure or porous layer or only extend to a certain depth. In an aspect, the macropores of the porous structure can have pores having a diameter of about 100 nm to 10,000 nm, a length of about 500 nm to 100,000 nm and a volume of 0.2-1 cc/g. In an aspect, the mesopores of the porous structure can have pores having a diameter of about 5 nm to 100 nm, a length of about 10 nm to 10,000 nm, and a volume of 0.5-2 cc/g. In an aspect, the micropores of the porous structure can have pores having a diameter of about 0.5 to 5 nm, a length of about 0.5 nm to 1000 nm and a volume of about 0.1-1 cc/g.

In an aspect, the surface of the porous structure can have porous walls that have a porosity of at least 90%, at least 85%, at least 80%, at least 75%, at least 70%, at least 65%, at least 60%, or about 60 to 90%. In some embodiments, the porous walls of the flow-through substrate have a surface area of 100 $m^2$/g or more, 150 $m^2$/g or more, 200 $m^2$/g or more, or 250 $m^2$/g or more.

In an embodiment, the porous substrate can include a surface layer on the surface of the pores of the substrate that can bond with the alkyl diamine-substituted aryl compounds. In an aspect, the surface layer can include organically modified moieties (e.g., alkyl groups, hydroxyl groups, carboxylate groups, amines, phosphoric acid, sulfonic acid, thiols, phosphines, and the like) on the surface (e.g., outside and/or inside surfaces of pores) of the material. In an embodiment, the surface layer can include surface alkyl groups hydroxyl groups, carboxylate groups, amines, phosphoric acid groups, sulfonic acid groups, thiols, phosphines, and the like, that the alkyl diamine-substituted aryl compounds can directly covalently bond and/or indirectly covalently bond (e.g., covalently bond to a linker covalently bonded to the material). In an embodiment, the surface layer can include an organic polymer having one or more of the following groups: alkyl groups, hydroxyl groups, carboxylate groups, amines, phosphoric acid groups, sulfonic acid groups, thiols, phosphines, and the like. In another embodiment, the structure can be a carbon support, where the carbon support can include one or more of the following groups: alkyl groups, hydroxyl groups, carboxylate groups, amines, phosphoric acid groups, sulfonic acid groups, thiols, phosphines, and the like.

In an aspect, the porous substrate can include a porous coating (also referred to as a "washcoat") on the surface of the substrate. In an embodiment, the porous coating can be a foam such as a polymeric foam (e.g., polyurethane foam, a polypropylene foam, a polyester foam, and the like), a metal foam, or a ceramic foam. In an aspect, the porous coating can include a metal-oxide layer such as silica or alumina on the surface of the substrate. In an aspect, the porous coating can be present on the surface of the substrate, within the pores or voids of the substrate, or a combination thereof. In an embodiment, the porous coating can be about 100 μm to 1500 μm thick and the pores can be of the dimension described above and herein. In an aspect, the porous substrate can be a porous substrate and can also include the porous coating on some or all parts of the porous substrate, where the alkyl diamine-substituted aryl compounds can be present in one or both of the pores of the porous substrate and the porous coating.

In an embodiment, the porous substrate can be a honeycomb structure such as a monolith honeycomb structure that includes channels. In an aspect, the monolith honeycomb structure can have a length and width on the order of cm to in while the thickness can be on the order of mm to cm or more. In an aspect, the monolith honeycomb structure does not have fibrous dimensions. In other words, the honeycomb structure can be a flow-through substrate comprising open channels defined by walls of the channels. In an aspect, the channels can have about 50 to about 900 cells per square inch, In an aspect, the channels can be polygonal (e.g., square, triangular, hexagonal) sinusoidal, circular, or the like, in cross-section. The length of the channels can be straight, zig-zag, skewed, or herringbone in shape and can have a length of 1 mm to 10s of cm or more. The channels can have walls that are perforated or louvered. In an aspect, the alkyl diamine-substituted aryl compounds can be disposed in the pores of the honeycomb structure and/or in the pores of a porous layer on the surface of the honeycomb structure.

In an embodiment, the honeycomb structure can comprise an inlet end, an outlet end, and inner channels extending from the inlet end to the outlet end. In some embodiments, the honeycomb comprises a multiplicity of cells extending from the inlet end to the outlet end, the cells being defined by intersecting cell or channel walls.

In an aspect, the honeycomb structure is ceramic (e.g., of a type produced by Corning under the trademark Celcort) that can be used with the alkyl diamine-substituted aryl compounds in accordance with the principles of the present disclosure, The alkyl diamine-substituted aryl compounds can be coated or otherwise immobilized on the inside of the pores of the ceramic honeycomb structure and/or within a porous layer on the surface of the ceramic honeycomb structure. In an aspect, the porous coating can include a metal-oxide layer such as silica or alumina on the surface of the substrate. In an embodiment, the metal-oxide layer can be mesoporous.

In another aspect, the present disclosure provides for methods of separating $CO_2$ from a gas mixture. The method can include exposing a gas mixture to a porous structure having supported therein an alkyl diamine-substituted aryl compound for a time frame of seconds to minutes to hours or longer. The gas mixture has a concentration of about 100 ppm to 20% of $CO_2$. The $CO_2$ in the gas mixture can be separated from the gas mixture by the porous structure and captured by the porous structure. The separation and capture can be conducted at atmospheric pressure and at a temperature of about −30° C. to 50° C. or about −20° C. to 50° C. After the gas mixture is exposed to the porous structure, the residual gas mixtures (e.g., with a lower $CO_2$ concentration that prior to exposure) can be diverted elsewhere or recirculated as needed. The capturing step can capture about 10% to 100% of the $CO_2$ present in the gas mixture. After a time-frame (e.g., hours to days), the porous structure can be treated to release the $CO_2$ from the porous structure in a controlled manner to be recycled, processed, or otherwise stored for disposal. The release can be conducted at atmospheric pressure and at a temperature of about 25° C. to 150° C. or about 60° C. to 150° C. In an aspect, the release can be performed by exposing the porous structure to steam, where the temperature of the steam is about 60° C. to 150° C. and the pressure of the steam is about 0.2 bara to 5 bara.

In regard to the ceramic substrates described herein, the ceramic substrates can form part of a system having elements for moving the monolithic ceramic substrates between a position where sorbent on the monolithic structure is exposed to ambient air from which $CO_2$ can be extracted by the sorbent, and a position where the sorbent can be regenerated and the $CO_2$ captured. This regeneration preferably is carried out in a sealed regeneration chamber, where the carbon dioxide-laden sorbent is exposed to process heat steam at a temperature not greater than 100-120° C.; the thus released $CO_2$ is withdrawn from the regeneration chamber for storage or further treatment.

Alternatively, the system can be a stationary bed of particulate porous material such as a ceramic held together in a support that is open to a flowing gaseous mixture but effective to hold the stationary bed in place when exposed to the gas flow, e.g., ambient air, to adsorb the carbon dioxide from the air, or when exposed to process heat steam to regenerate the sorbent and release the carbon dioxide. Such individual discrete particles can include a powder, an extrudate particle, flakes or spheres.

The individual particles can also form a moving bed where the individual particles are moved either by gas flow or by a moving belt for example between a position where they will be exposed to a gas mixture containing carbon dioxide and a position where the sorbent is regenerated and the freed carbon dioxide is captured for further storage or processing.

Such particulate forms of the substrate can be utilized regardless of the materials forming the particles, but the particles are preferably formed of a ceramic, a metal, or a metal oxide in such cases.

EXAMPLE

Now having described the embodiments of the sorbents in general, the Examples describe some embodiments of the sorbents and uses thereof. The following is a non-limiting illustrative example of an embodiment of the present disclosure that is not intended to limit the scope of any embodiment of the present disclosure, but rather is intended to provide some experimental conditions and results. Therefore, one skilled in the art would understand that many experimental conditions can be modified, but it is intended that these modifications be within the scope of the embodiments of the present disclosure.

Example 1

The increase in atmospheric $CO_2$ concentration has alarming implications for global climate change. Intense efforts have been dedicated by researchers to develop effective technologies for carbon capture and sequestration (CCS), with an approach recently recognized as potentially critical to rapid climate stabilization, the direct removal of $CO_2$ from the atmosphere, or direct air capture.[1-3] Direct air capture of $CO_2$ (DAC) from the atmosphere has been recently developed as a potential negative emissions technology (NET) due to its technological, scalability and environmental advantages.[4-7]

One technology explored in the recent years for DAC applications uses solid-supported amine adsorbents, especially for their $CO_2$ adsorption performance at low temperature.[2, 4, 8-9] Based on the sorbent processing approach, these materials have been grouped into three classes. Class 1 sorbents consist of small molecules and polymeric amines that are physically confined into porous supports.[4, 10-11] Small molecules, usually aminosilanes, covalently bound to the inner and exterior porous support surface form the class 2 materials.[12-15] While the class 1 sorbents exhibit higher $CO_2$ adsorption capacity than the class 2 materials in many cases due to higher amine loadings, impregnated amines may be more mobile during sorbent regeneration and also may be less stable towards leaching or volatilization.[16-20] Combining covalent immobilization and use of polymeric amines led to the class 3 materials.[21-22] The process typically uses in-situ polymerization of amine-containing monomers inside the support pores and yields highly stable oligomeric and polymeric amine-rich species covalently bound to the solid's walls. More recently, efforts have been focused on developing polymeric materials that exhibit combined properties of both solid supports and amine adsorbents.[3, 23-24] Despite these varied approaches developed till date, the library of the amine sorbents needs to be further expanded to new compounds that render improved $CO_2$ capture performance, thermal/oxidative stability and low synthesis cost. A particular aspect of interest is the design of polyamine architectures that display the amine groups in such a way to facilitate easy access by adsorbing and desorbing gas species.

To this end, we note that benzene substituted with various functional groups is an appealing core for the preparation of star-like small molecules and polymers. Sun et. al prepared a series of polymers by facile nucleophilic substitution reactions using inexpensive and readily available 2,4,6-tris(chloromethyl)mesitylene (TCM) and diamine monomers.[25-26] Generally amines are adequately nucleophilic to allow for direct alkyl halide alkylation, and the reaction can be carried out under mild conditions without any catalyst. Two patent applications by Looper et al. have described methods for preparing a variety of polyamines containing an aromatic core anchored by one, two and three amine-rich side arms.[27-28] Targeting the biocidal activity of the polymers, the authors have used a three-step synthesis that, in the case of some products, required protection of one terminal primary amine of spermine and of its polyamine homologues. In addition, the preparation also required the use of metal catalysts (e.g. Pd) and pyrophorics (e.g. NaH).[27] In another multi-step approach. Stawicki et al. have reported dipodal and tripodal amine scaffolds that were subsequently used to prepare ligand adducts for in-vivo uranyl removal. For the preparation of these amines, the authors reacted bis- and tris-bromo-methyl-aryl derivatives with excess diamine (e.g. ethylenediamine, 1,3-propylenediamine, 1,4-butandiamine).[29] One of the simplest and most promising approaches to decreasing the process costs of solid-based DAC is to use alkyl amine molecules or macromolecules as class 1 sorbents. The most commonly used method for preparation of these composite materials is solution impregnation leading to both physical binding of amine molecules to the substrate surface and partial or complete pore filling.[30-31] Depending on their porosity, solid supports are able to carry varied amounts of amine content.[31-33] Mesoporous silicas,[10, 34] alumina,[35] zeolites,[13] graphene oxide,[36] porous polymers,[37] carbons,[38] MOFs,[39] and carbon nanotubes[40] are a few examples of supports investigated for extending the library of amine-containing composite materials for $CO_2$.[41-44] These supports can often preserve the thermal stability and prolong the lifetime of amine sorbents because of their improved stability under ambient and elevated temperature conditions.

Porous amine polymers have also been studied as single component sorbents not requiring a separate non-polymeric support phase. As examples, Zhou et al. reported a series of polyamines-tethered porous polymer network (PPN) materials for $CO_2$ capture. PPN tethered with diethylenetriamine (PPN-6-$CH_2$DETA) showed the highest $CO_2$ uptake of 4.3 mmol $g^{-1}$ at 295K under flue gas conditions when compared to other materials reported in the study.[45] In another study, PPN-6-$CH_2$DETA was investigated for $CO_2$ capture from air, in which the amine grafted PPN showed a high $CO_2$ capacity of up to 1.04 mol/kg as calculated from ideal adsorption solution theory.[46]

In addition to enabling a decrease in materials costs, new sorbents should ideally equal or surpass the adsorption abilities of the more widely used amine materials such as poly(ethyleneimine) (PEI).[2, 19, 31] Branched and linear PEI have a high content of aliphatic primary and secondary amine groups that are ideal for capturing $CO_2$. Various research groups have studied linear and branched PEI impregnated into mesoporous materials for $CO_2$ capture both from DAC and flue gas.[2, 10, 47-48] Regardless of the molecular architecture, e.g. linear vs branched, the adsorption capacity depended on the PEI molecular weight.[49] However, PEI is affected by oxidation when exposed to conditions simulating a process upset, combining high oxygen partial pressures and elevated temperatures, more oxidatively stable sorbents have been sought.[50-52] For example, Bali et al. reported that PAA based adsorbents were more stable than branched PEI counterparts at elevated temperatures (110° C.) and high $O_2$ concentrations (21%) during humid oxidation conditions.[53] Later in 2017, Wang et al. reported composite materials made by infusing SBA-15 with poly(allylamine) (PAA) and compared with SBA-15 supported PEI sorbents.[54] The best $CO_2$ adsorption performance was achieved at 65% PAA loading (109 mg $CO_2$/g) at 140° C. and 10% $CO_2$ stream. Recently, linear poly(propyleneimine) (l-PPI) was prepared and determined to be a more oxidatively stable sorbent than benchmark PEI-based materials. Composite materials of l-PPI, ranging from 700 Da to 36,000 Da in molecular weight, loaded on an SBA-15 support were more efficient at $CO_2$ capture than linear PEI/SBA-15 homologues in a 400 ppm $CO_2$ stream, and they retained 65-83% of their $CO_2$ capacity after harsh oxidative treatment.[55] In contrast, only 20-40% retention was recorded for linear PEI/SBA-15 under similar conditions. In addition, branched PPI prepared by ring-opening polymerization of azetidine was also found as a promising alternative to PEI-based adsorbents.[56-57]

We hypothesize that the impregnation of alkyl-aryl small molecules incorporating aliphatic repeat units akin to PEI and PPI into various mesoporous substrates would yield composite materials that may exhibit better thermal and oxidative stability than PEI, the benchmark amine polymer used in prototype DAC and post-combustion capture technologies, with better $CO_2$ uptake capacities. In this example, alkyl-aryl small molecules (Ph-X-YY) were prepared by one-step nucleophilic substitution from tri- (X=3) and hexa-bromine-substituted (X=6) aromatic cores with two different aliphatic diamines, ethylenediamine (YY=ED) and, 1,3-propylenediamine (YY=PD), respectively. Synthesis of Ph-X-YY was confirmed by $^1$H and $^{13}$C NMR, Ph-X-YY alcoholic solutions of various concentrations were combined with the SBA-15 silica support to yield Ph-X-YY/SBA-15 composite materials. Their amine loading was evaluated from both thermogravimetric and elemental analysis assays. The porosity characteristics of the impregnated support were determined by nitrogen physisorption. Noting that many of the amine sorbent examples cited above that appear to have high uptake capacities were tested under conditions that may not be relevant to practical carbon capture, for example using pure $CO_2$ and/or very low temperatures, the $CO_2$ adsorption performance under dry (400 ppm $CO_2$ at 35° C.) and humid conditions (30% humidity, 400 ppm at 35° C.) were evaluated by thermogravimetric analysis and via a fixed bed, breakthrough set up, respectively. Control PEI/SBA-15 samples were used as well. To assess the impact of long-term use under conditions similar to DAC, the Ph-X-YY/SBA-15 sorbents were subjected to temperature-swing cycles and accelerated oxidation treatments (21% $O_2$/He). The findings of the study suggest that Ph-X-YY/SBA-15 composite materials are promising platforms for use in DAC technology.

EXPERIMENTAL SECTION

Synthesis of alkyl-aryl amine-rich molecules (Ph-X-YY): Detailed experimental procedures for the synthesis of all the alkyl-aryl amine-rich molecules Ph-3-ED, Ph-3-PD, Ph-6-ED, Ph-6-PD, and the characterization data (NMR and HR-MS) are provided in the Supporting Information (SI). The Ph-X-YY molecule abbreviation means Ph—phenyl moiety, X—degree of substitution of the phenyl ring (3 or 6) and YY—diamine substituents, ED (ethylene diamine) or PD (propane-1,3-diamine).

Synthesis of mesoporous silica SBA-15: SBA-15 was synthesized as reported previously by Pang et al.[11]

Preparation of Ph-X-YY/SBA-15 composites: Ph-X-YY/SBA-15 composite materials with various loadings of Ph-X-YY were prepared using the wet impregnation method.[11] Details can be found in the Supporting Information (SI).

Detailed experimental procedures for $CO_2$ capture, temperature swing cycling, and oxidation studies using a TGA and humid fix bed breakthrough system are provided in the supporting information (SI).

Results and Discussion:

Synthesis and Characterization of Alkyl-Aryl Amine-Rich Molecules (pH-X-YY):

Scheme 1. Reaction scheme for the synthesis of aryl-alkyl amine reach molecules (Ph-X-YY).

Ph-3-YY-Series

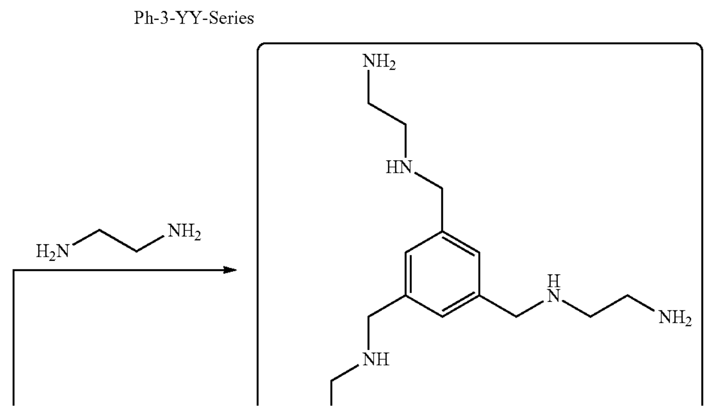

-continued
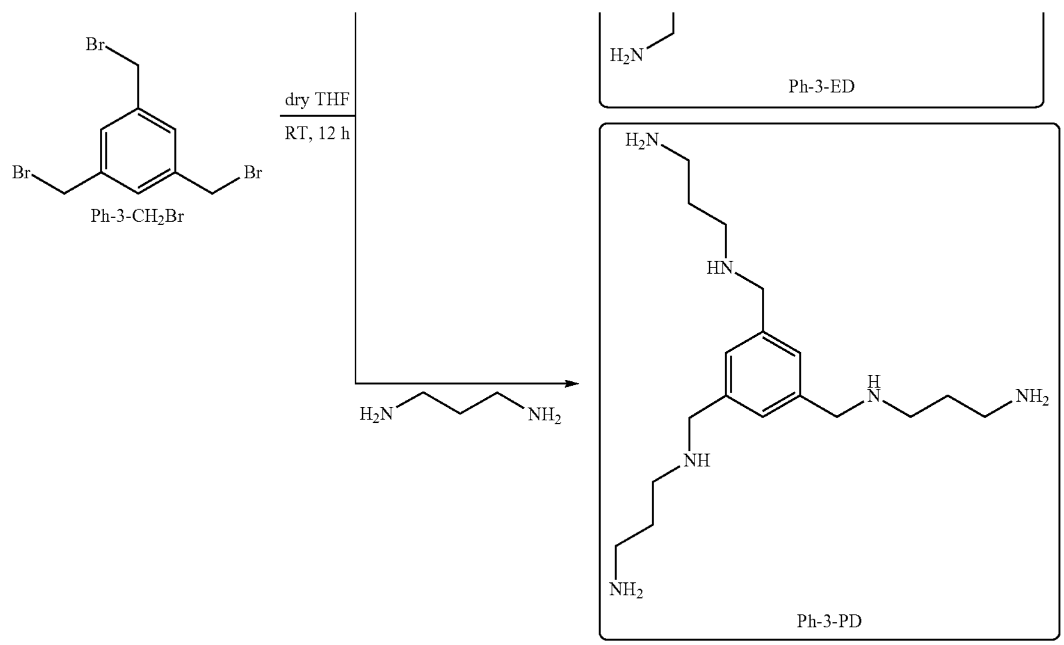
Ph-6-YY Series
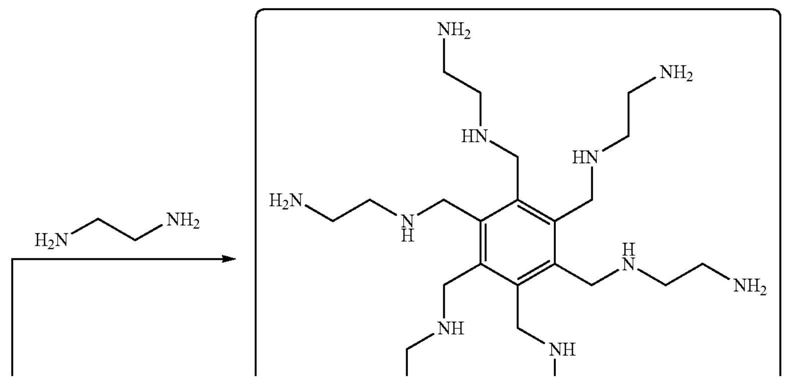

-continued

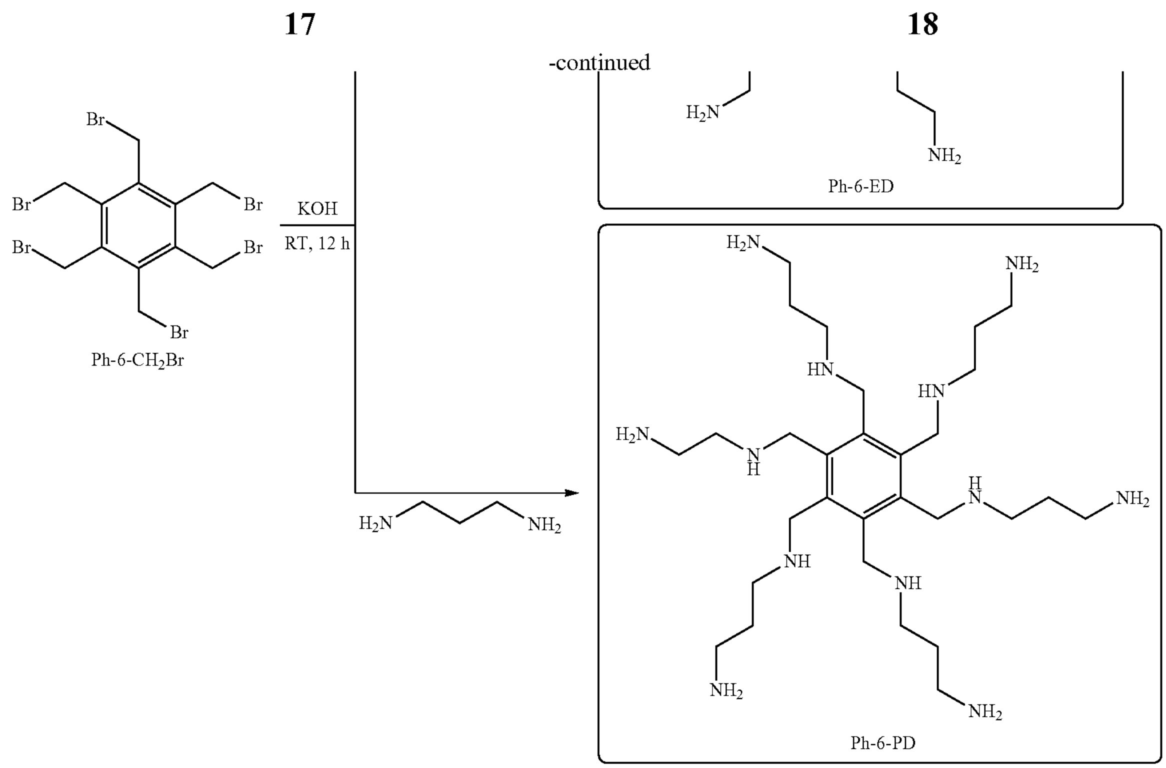

Tri- and hexa-amine substituted benzene molecules were synthesized by the one-step nucleophilic substitution between commercially available bromomethyl-substituted benzene and excess diamines.[29] As shown in Scheme 1, for the Ph-3-ED synthesis, 1,3,5-tris(bromomethyl)benzene (Ph-3-$CH_2$Br) was reacted with excess ethylenediamine (ED) by using THF as a solvent, while Ph-3-PD required reacting the Ph-3-$CH_2$Br and excess propane-1,3-diamine (PD). In the case of Ph-6-ED and Ph-6-PD, the synthesis was performed by using the same diamines (ED and PD) and hexakis (bromomethyl)benzene (Ph-6-$CH_2$Br). The use of excess diamine and slow addition of the aromatic precursor solution were required to prevent oligomerization/polymerization in some cases. All four synthetic routes produced a high yield (60-90%) of products. Conceivably, lower yields observed for the Ph-6-YY series when compared to Ph-3-YY could be due to the formation of oligomers and polymers. The purification method based on precipitation-filtration likely removed species other than single molecules due to their different solubilities. The preparation of the Ph-X-YY molecules was confirmed by NMR in deuterated water ($D_2O$). The $^1$H NMR spectrum of Ph-3-ED showed three protons of the phenylene ring appearing as singlets at 7.21 ppm. The proton signal of the methylene group directly connected to the phenyl ring appeared as singlet centered at 3.73 ppm. A pair of triplets centered at 2.61 and 2.71 ppm were assigned to methylene protons belonging to the alkyl chain of the diamine: one connected to the secondary amine and the other one to the primary amine, respectively. In addition, HR-MS of the Ph-3-ED gave the m/z ratio as 295.2607 (calc. 295.2605). The $^1$H NMR spectrum of Ph-3-PD showed similar peaks as compared to that of Ph-3-ED except for the peak observed at 1.65 ppm associated with the additional methylene protons. HR-MS of the Ph-3-PD gave an m/z ratio of 337.3078 (calc. 337.3074). As expected, the $^1$H NMR spectra of Ph-6-ED and Ph-6-PD did not show any phenyl protons due to full substitution with the two diamines. Methylene protons directly connected to the phenyl ring were observed at ~3.8 ppm for Ph-6-ED and Ph-6-PD, as observed for Ph-3-YY (~3.72 ppm). For Ph-6-ED, the methylene protons between the primary and secondary amines were observed as a multiplet (2.75-2.85 ppm). In contrast, for Ph-6-PD, two triplets were observed centered at 2.67 and 2.77 ppm for the methylene protons directly connected to the primary and secondary amines. ESI-MS of the Ph-6-ED showed the molecular ion at 511.4663 (m/z) (511.4667 calc.) and that of the Ph-6-PD at 595.5602 (m/z) (595.5606 calc.).

Characterization of the Ph-X-YY/SBA-15 composites: The Ph-X-YY/SBA-15 composites were prepared by the wet impregnation method.[55, 58] The resulting composites were further subjected to thermogravimetric analysis (TGA) to assess the fraction of organic content (aka Ph-X-YY). These values were evaluated from the 120° C.-900° C. temperature interval, as shown in FIGS. 7A-7D. The actual organic loadings obtained by TGA were close to the calculated target loadings used in sample preparation. DSC measurements performed in parallel to TGA indicated that the impregnation of Ph-X-YY molecules into mesoporous silica SBA-15 led to improved thermal stability when compared to the unsupported alkyl-aryl amine-rich molecules (FIGS. 8A-8D). The increase in thermal stability of Ph-X-YY/SBA-15 composites was likely due to van der Waals forces, H-bonding and/or dipole interactions between the alkyl-aryl amine-rich molecules and OH groups present in silica support.[59] π-π stacking between aryl units may also impart some stability. The elemental analysis (EA) of Ph-X-YY/SBA-15 samples showed an increase in the amine loading (mmol N/g $SiO_2$) with the targeted increases in organic loading (Table S1).

$N_2$ physisorption is widely used to investigate the porosity of materials,[11, 55-56, 58, 60] and was used here to determine the pore structural parameters of the mesoporous SBA-15 before and after impregnation with Ph-X-YY molecules (FIG. 1, FIGS. 9A-9D, and Table S1). The pore volume, the pore size distribution and the surface area of SBA-15 and Ph-X-YY/SBA-15 composites were determined using the Brunauer-Emmett-Teller (BET) and Barrett-Joyner-Halenda (BJH) methods (Table S1). Bare SBA-15 had an average pore diameter of ~7 nm accounting for a total pore volume of 0.96 $cm^3/g$. As expected, after impregnation with Ph-X-YY, the volume of nitrogen uptake decreased drastically, indicating that the pores became smaller due to the presence of the Ph-X-YY molecules. As shown in FIG. 1A the total pore volume of the 20% Ph-3-ED/SBA-15 composite decreased from 0.96 to 0.71 $cm^3/g$ (26% pore filling). An increase of 30, 40, 50 and 60% in organic content was reflected in a further decrease in pore volume to 0.59, 0.41, 0.18 and 0.01 $cm^3/g$, respectively. These values correspond to a pore filling percentage of 39, 57, 82 and 97%, respectively. The reduction in the total pore volume and pore size of the SBA-15 was correlated to the increase in organic loadings, as also observed in TGA. The same trend was observed in amine content, as evaluated by elemental analysis. The amine loadings in the Ph-3-ED/SBA-15 composites increased from 3.3 at 20% loading to 16.7 mmol $N/g_{SiO2}$ at 60% loading, coinciding with the increasing Ph-3-ED loading in the pores of SBA-15 (Table S1). A similar incremental trend in pore filling and amine loading was also observed for Ph-3-ED/SBA-15 composites. (FIG. 9A-9D). The calculated pore filling values for Ph-3-PD/SBA-15 composites at 20, 30, 40 and 50% organic loading were 20, 40, 61 and 90%. Following the same trend, the amine content increased from 3.94 to 12.45 mmol $N/g_{SiO2}$ (Table S1).

$N_2$ physisorption analysis of the Ph-6-YY/SBA-15 composites also shows similar incremental trends in pore filling like that of Ph-3-YY/SBA-15 composites except that the values were higher at the same organic loadings. With similar organic loading in case of Ph-3-YY (20%, 30%, 40% and 50%), Ph-6-ED composite shows 34%, 55%, 77% and 94% pore filling (FIG. 1). As expected in case of Ph-6-ED (4.54-16.7 mmol $N/g_{SiO2}$) and Ph-6-PD (4.23-15.48 mmol $N/g_{SiO2}$), a higher amine loading range was observed due to higher degree of substitution of the aromatic core with diamine moieties (FIG. 9A-9D and Table S1). FIGS. 1B and 1D displays the average pore size variation (~5-7 nm) of these composite materials.

Another parameter that confirmed successful impregnation of Ph-X-YY into the SBA-15 supports was the specific surface area. As listed in Table S1, the BET surface area of bare SBA-15 was 700 $m^2/g_{SiO2}$. In general, the variation of this parameter for the composite samples was in the range of 400-30 $m^2/g_{SiO2}$, following the trend in pore filling (20-90%). As expected, the slightly smaller specific surface area and slightly higher total pore filling was observed in case of Ph-6-YY, as compared to the Ph-3-YY, is due to the fact that Ph-6-YY molecules are bulkier and occupy a larger volume. Previously, Holewinski et al. studied the distribution of branched poly(ethylenimine) (b-PEI) in the pores of mesoporous SBA-15 using $N_2$ physisorption and small-angle neutron scattering (SANS). In this study, it was concluded that initially at lower loadings PEI forms a thin conformal coating around the pore walls and successively at higher loading, PEI aggregates into plug(s) that grow along the pore axis.[61] Later, similar pore filling behavior was also confirmed by using linear PPI/SBA-15 composites using $N_2$ physisorption isotherms.[11, 55] Overall, the combined results obtained from organic TGA, EA and $N_2$ physisorption isotherms of Ph-X-YY/SBA-15 composites show similar pore filling behavior with an increase in organic and amine loading as compared with PEI and PPI. Together the data indicate that Ph-X-YY molecules were distributed within the cylindrical mesopores of the silica hosts. The wet impregnation method is an effective technique to impregnate alkyl-aryl amine-rich molecules into mesoporous SBA-15 with well-controlled loading.

Figures 2A, 2B, 3A, 3B:
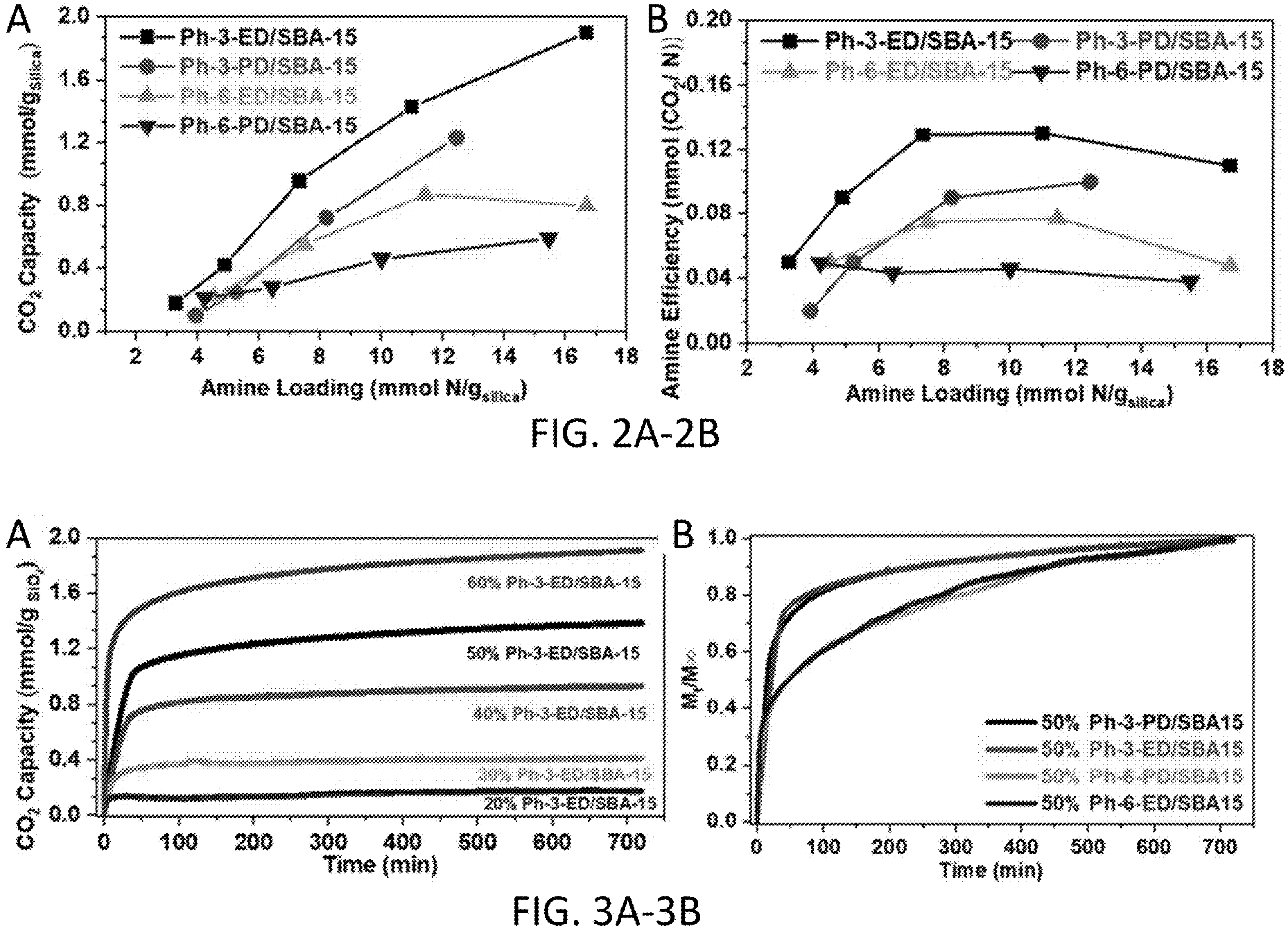
FIG. 2A illustrates $CO_2$ adsorption capacity and FIG. 2B illustrates amine efficiencies recorded for Ph-3-ED, Ph-3-PD, Ph-6-ED, and Ph-6-PD supported with SBA-15 as a function of amine loading at 35° C. under dry 400 ppm $CO_2$/He exposure conditions.
FIG. 3A illustrates $CO_2$ uptake profiles for (20%-60%) Ph-3-ED/SBA-15 and FIG. 3B illustrates the comparison of normalized dynamic $CO_2$ uptake profiles for 50% Ph-3-ED/SBA-15, 50% Ph-3-PD/SBA-15, 50% Ph-6-ED/SBA-15 and 50% Ph-6-PD/SBA-15. Adsorption conditions: 35° C. for 12 h under 400 ppm $CO_2$/He.

$CO_2$ capacity and amine efficiency of Ph-X-YY/SBA-15 under dry 400 ppm $CO_2$ exposure conditions: The $CO_2$ adsorption performance of the Ph-X-YY/SBA-15 composites under dry $CO_2$ conditions was investigated gravimetrically by thermogravimetric analysis (TGA). After isothermal pretreatment at 110° C. to remove adsorbed water and $CO_2$ adsorbed from the atmosphere, the $CO_2$ adsorption was performed at 35° C. for 12 h under dry 400 ppm $CO_2$ balanced with helium ($CO_2$/He). As shown in FIG. 2A, the $CO_2$ capacity increased with the amine loading for all the Ph-X-YY/SBA-15 composites. Regardless of the amine loading, Ph-3-ED/SBA-15 and Ph-3-PD/SBA-15 materials showed superior $CO_2$ adsorption capacities than their Ph-6-ED/SBA-15 and Ph-6-PD/SBA-15 homologues. For example, at 40% loading they reached 1.43 mmol $CO_2/g_{SiO2}$ and 1.23 mmol $CO_2/g_{SiO2}$ versus 0.87 mmol $CO_2/g_{SiO2}$ and 0.46 mmol $CO_2/g_{SiO2}$, respectively. These values were achieved at an amine loading of ~12 mmol $N/g_{SiO2}$. The highest uptake, 1.9 mmol $CO_2/g_{SiO2}$, was recorded for 60% Ph-3-ED/SBA-15 at an amine loading of 16.7 mmol $N/g_{SiO2}$. The highest $CO_2$ capacity obtained for 60% Ph-3-ED/SBA-15 sorbent was closely comparable to that of the previously studied 50% linear PPI ($M_w$=700-36000 Da)/SBA-15 (~2.1 mmol/$g_{SiO2}$)[55] and higher than linear PEI ($M_n$=2500 Da and 25000 Da)/SBA-15 (1.25 mmol/$g_{SiO2}$),[5] dendritic PEI/SBA-15 (1.43 mmol/$g_{SiO2}$)[11] and 45% poly (glycidyl amine) (PGA)/SBA-15 (0.66 mmol/$g_{SiO2}$)[62] under the same adsorption conditions.[1, 55] However, the maximum $CO_2$ capacity falls short when compared with the branched 55% PEI ($M_w$=800 Da)/SBA-15 (3.04 mmol/$g_{SiO2}$) and 40% dendritic PPI/SBA-15 (2.64 mmol/$g_{SiO2}$) materials.[11]

On the other hand, the calculated amine efficiencies shown in FIG. 2B increase only up to ~8 mmol $N/g_{SiO2}$ amine loading after which became constant and then decreased. For example, 30% Ph-3-ED/SBA-15 displayed the highest amine efficiency, 0.13 mmol $CO_2$/mmol N at 7.3 mmol $N/g_{SiO2}$ loading, a value that was essentially constant up to 40% loading sample at 11 mmol $N/g_{SiO2}$ loading. Despite adsorbing the largest amount of $CO_2$, the amine efficiency of 60% Ph-3-ED/SBA-15 was only 0.11 mmol $CO_2$/mmol N. The 50% Ph-3-PD/SBA-15 sample had slightly lower values, 0.1 mmol $CO_2$/mmol N, but these were higher than that of 50% Ph-6-ED/SBA-15 (0.048 mmol $CO_2$/mmol N) and 50% Ph-6-PD/SBA-15 (0.046 mmol $CO_2$/mmol N). Interestingly, 50% Ph-6-PD/SBA-15 showed a flat average value of ~0.045 mmol $CO_2$/mmol N, irrespective of the amine loading, which is unusual for amine-loaded materials. These trends, except that of 50% Ph-6-PD/SBA-15, are consistent with those observed for linear PPI and PEI.[55] Together, the $CO_2$ adsorption capacity and amine efficiency data indicate that full substitution of the aromatic ring with amine-containing arms does not favor higher performance, likely due to the bulky molecular structure. The maximum amine efficiency obtained for 50% Ph-3-ED/SBA-15 (0.13 mmol $CO_2$/mmol N) is comparable to the maximum amine efficiency reported for other studied materials such as linear PEI ($M_w$=2500 Da) (0.07 mmol $CO_2$/mmol N), 55% branched PEI (800 Da) (0.13 mmol $CO_2$/mmol N) and 50% linear PPI (700 Da) (0.15 mmol $CO_2$/mmol N).[55, 62]

Figures 10A, 10B:
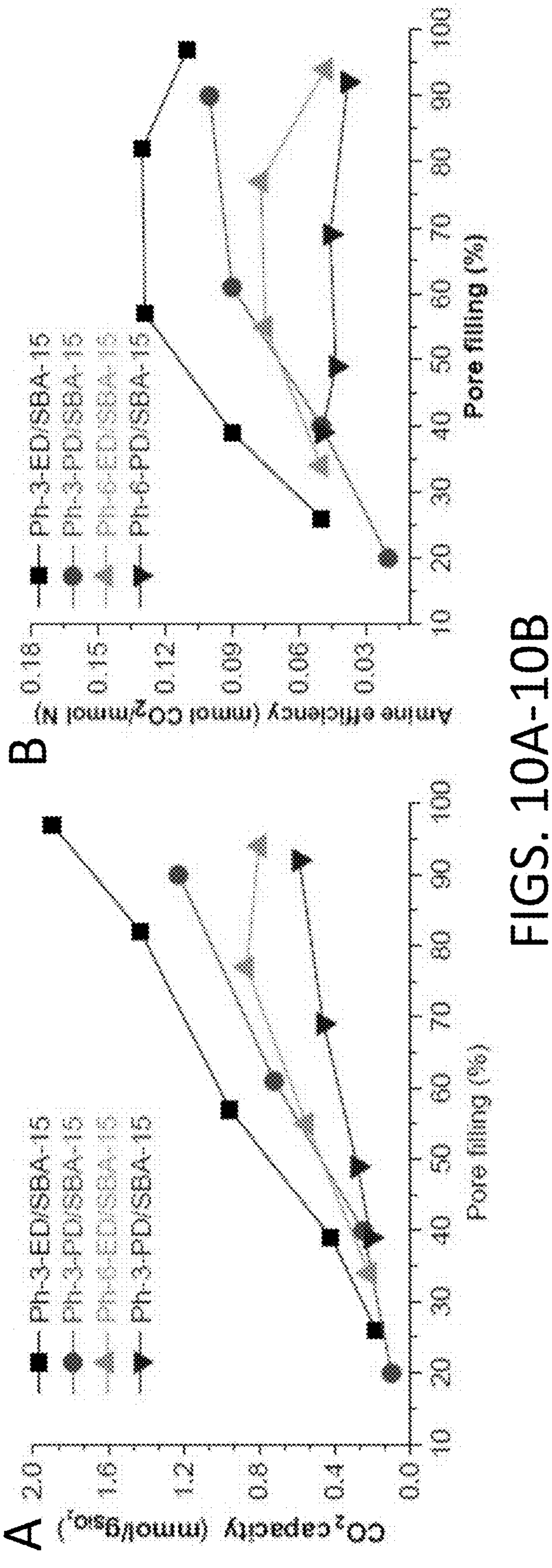
FIG. 10A illustrates $CO_2$ capacity and FIG. 10B illustrates amine efficiency for Ph-3-ED/SBA-15, Ph-3-PD/SBA-15, Ph-6-ED/SBA-15, and Ph-6-PD/SBA-15 as a function of pore filling.
Figures 11A, 11B, 11C, 11D:
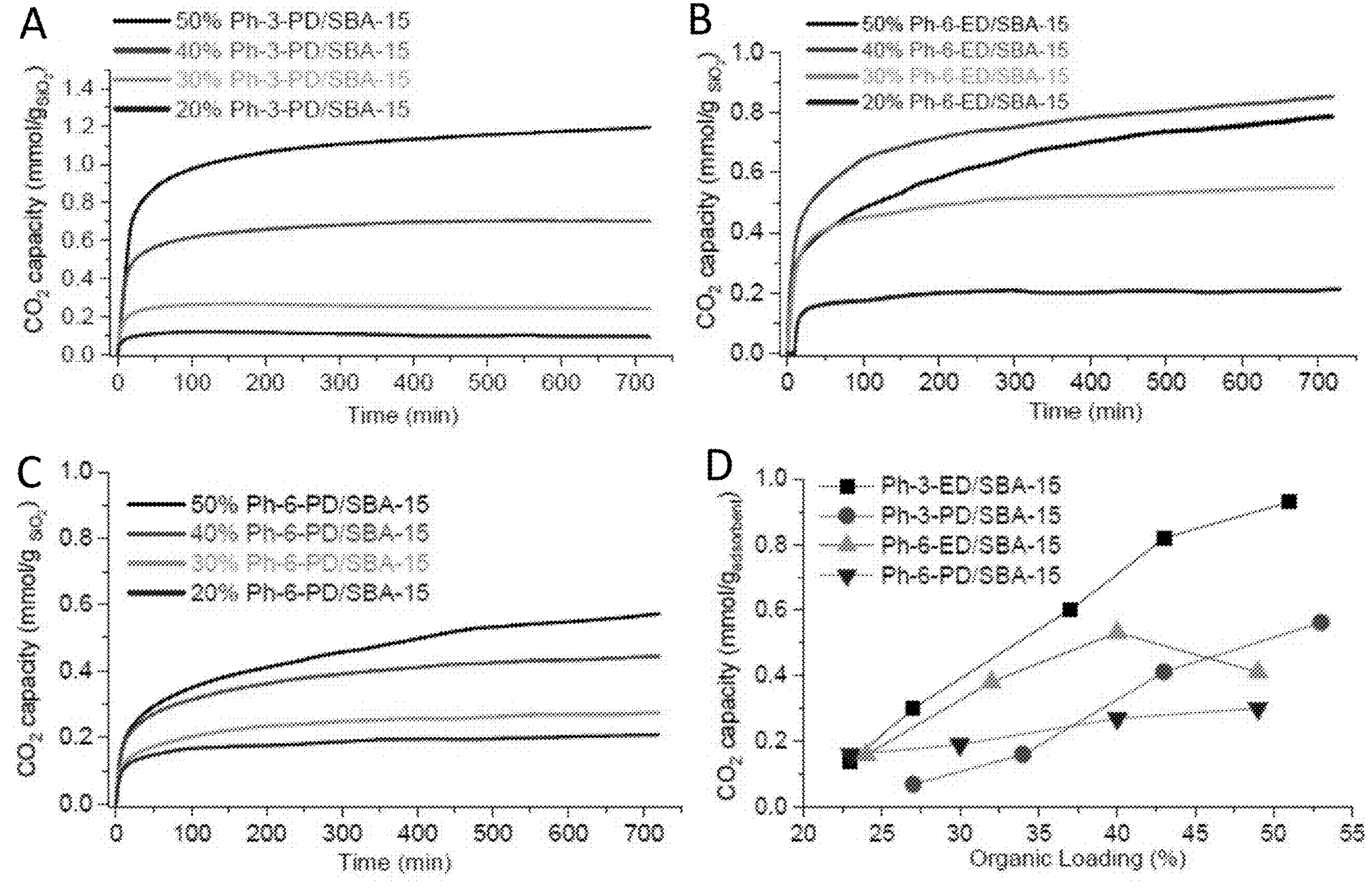
FIGS. 11A-11D illustrate $CO_2$ uptake profiles (mmol/$g_{SiO2}$) for (FIG. 11A) Ph-3-PD/SBA-15, (FIG. 11B) Ph-6-ED/SBA-15, (FIG. 11C) Ph-6-PD/SBA-15 and (FIG. 11D) $CO_2$ adsorption capacity (mmol/$g_{adsorbent}$) recorded for Ph-3-ED, Ph-3-PD, Ph-6-ED, and Ph-6-PD supported with SBA-15 as a function of TGA organic loading (%) at 35° C. under dry 400 ppm $CO_2$/He exposure conditions.

The correlation with the pore parameter analysis underline the influence of Ph-X-YY molecular structure differences on $CO_2$ capture performance and amine efficiency. FIG. 10A-10B shows that Ph-3-ED/SBA-15 and Ph-3-PD/SBA-15 filled the pores up to 80-90% at 50% organic loading and adsorbed the largest amount of $CO_2$. While the pore filling values of 50% Ph-6-ED/SBA-15 and 50% Ph-6-PD/SBA-15 composites were slightly higher (≥90%), their $CO_2$ adsorption performance was significantly lower (FIG. 10A). The trend in amine efficiency (FIG. 10B) as a function of pore-filling followed the same pattern as the $CO_2$ uptake profiles. Apart from this tendency and similarly to the above data displayed in FIG. 2B, Ph-6-PD/SBA-15 presented a relatively constant average value around 0.04 mmol $CO_2$/mmol N. Likely due to their less bulky molecular architecture, Ph-3-YY molecules have the ability to better arrange and fill the voids of the SBA-15 support. The arrangement of these molecules may also involve intermolecular interactions of their π-system[63] coupled to less steric hindrance, enabling efficient exposure of a large number of amine sites to $CO_2$ gas molecules via diffusion. In the case of Ph-6-YY, the bulky nature hinders $CO_2$ access to amine groups due to steric hindrance.

To better understand the correlation between $CO_2$ uptake values at pseudoequilibrium at different amine loadings with time, the adsorption kinetic curves were compared, as shown in FIG. 3A and FIGS. 11A-11D. For all samples, the equilibrium capacities listed in Table S1 showed that the amount of $CO_2$ increased with the amine loading during the allocated 12 h adsorption time. The curves displayed an initial fast linear $CO_2$ uptake and approach to a maximum value of $CO_2$ adsorption then flattened to a pseudoequilibrium capacity for low organic contents (20% and 30%). On other hand, with higher organic loading (40%, 50%, and 60%) the curves also had a rapid initial increase, but then did not show a perfect plateau, rather presenting a slow and continuous slight increase in $CO_2$ uptake with time. In the low loading regime, the 30% Ph-6-ED/SBA-15 sample apparently had a slightly better performance than the 30% Ph-3-ED/SBA-15 counterpart (FIG. 11A-11D). This trend was more evident at 20% organic loading. An interesting behavior was noted for the 50% Ph-6-ED/SBA-15 sample: the linear approach to pseudo-equilibrium was slower than that shown by the 40% Ph-6-ED/SBA-15 homologue. In contrast, the 60% Ph-3-ED/SBA-15 displayed the fastest kinetics. These data also support the idea that the molecular structures of these two types of alkyl-aryl compounds dictate their $CO_2$ adsorption properties.

Additional evidence that the molecular architecture is a factor that governs $CO_2$ adsorbtion kinetics was obtained from plotting the normalized dynamic $CO_2$ uptake curves for 50% Ph-X-YY/SBA-15 composites (FIG. 3B). The shape of the two regions in the kinetic curves indicated that Ph-6-YY/SBA-15 samples show slower kinetic behavior than their Ph-3-YY/SBA-15 homologues. As also described above, Ph-3-YY/SBA-15 composites had better $CO_2$ sorbing abilities than Ph-6-YY/SBA-15 composites. Coupling these results with the trends seen in amine efficiency as a function of amine loading (FIG. 2B) and pore-filling (FIGS. 10A-10D) it is evident that the bulky molecular architecture of Ph-6-YY was a key parameter that hampered the Ph-6-YY/SBA-15 composite $CO_2$ performance, due to streric constraints within the molecule.

The shape of the kinetic curves demonstrates that the adsorption process reaches ~75% (Ph-3-YY) and ~50% (Ph-6-YY) of pseudoequilibrium $CO_2$ capacity in first 40 min (FIG. 3B). In the adsorption process, $CO_2$ molecules diffuse and form covalent and physical bonds with the amine sites. The result of these interactions is often the formation of an ammonium carbamate ion pair. The stabilization of the carbamate adduct can create intra and intermolecular crosslinks between two amine sites. Saturation of amine sites with $CO_2$ at 20% and 30% organic loading most likely does not lead to strong diffusional limitations, owing to limited pore filling by the amine molecules. At high amine loadings, however, the packing of amine molecules at the walls, especially within the pores, and the confinement conditions within the pores, can strongly influence the rate at which $CO_2$ establishes contact with free amine sites, thereby establishing intra/intermolecular crosslinks. The progressive cross-linking to stabilize the carbamate adduct can limit diffusion of $CO_2$ through the developing network resulting in slow kinetics after ~40 min, as shown in FIG. 3, FIG. 10B and FIG. 10C. Slower uptake kinetics at higher amine loadings were reported for various amine sorbents, including the benchmark poly(ethylenimine)[64-65] and recent reports on poly(propylenimine),[11, 55] and this has been suggested to be due to the agglomeration of the amine-containing organic phase in a bulk, liquid-like phase inside the pores.[66]

Figures 4A, 4B, 5A, 5B:
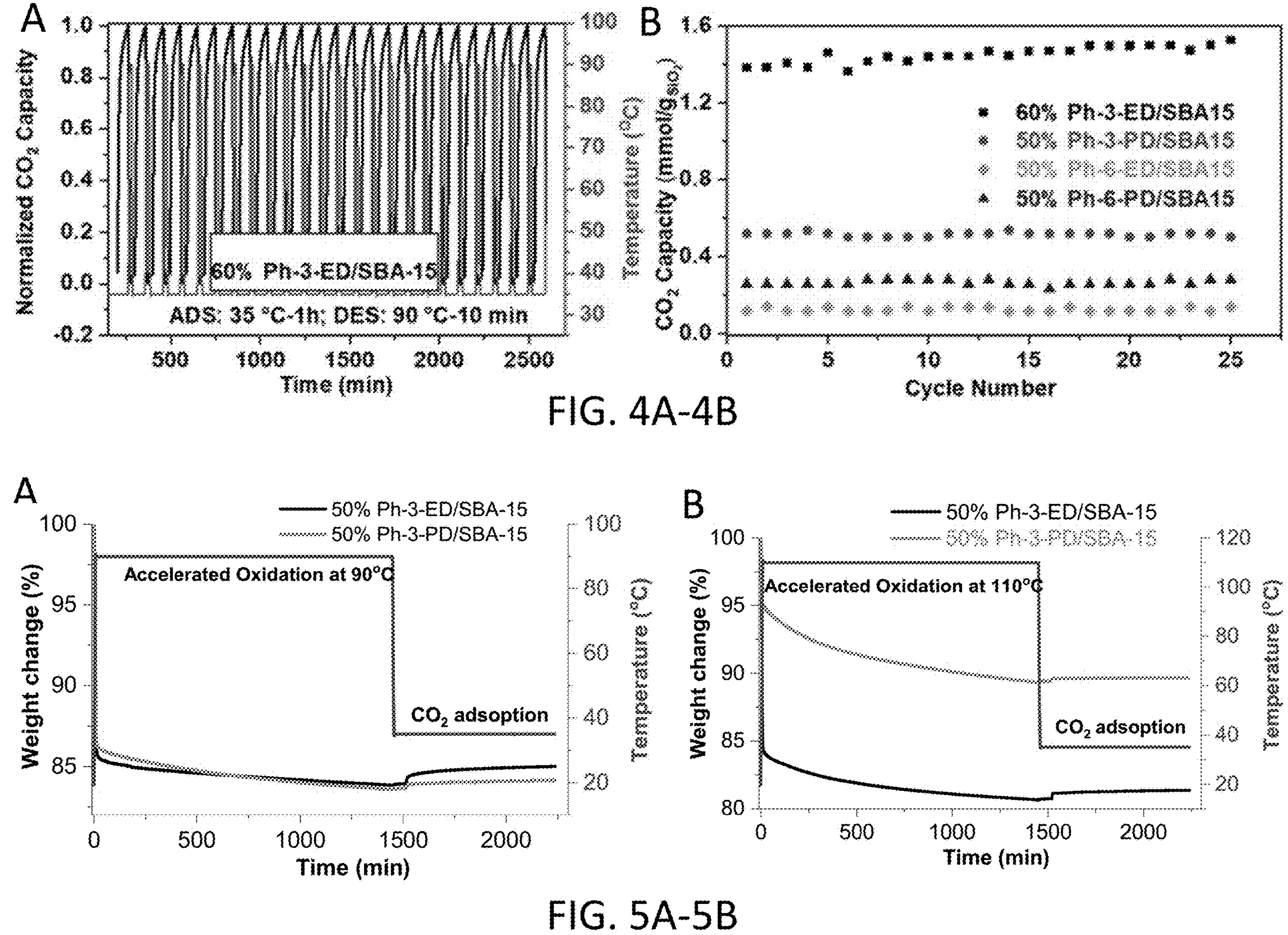
FIGS. 4A and 4B illustrate $CO_2$ adsorption/desorption temperature-swing profile for the (FIG. 4A) 60% Ph-3-ED/SBA-15 (normalized $CO_2$ uptake plot) and (FIG. 4B) $CO_2$ capacity calculated from the temperature-swing adsorption profiles for Ph-3-ED/SBA-15 (1.4 mmol/$g_{SiO2}$), Ph-3-PD/SBA-15 (0.5 mmol/$g_{SiO2}$), Ph-6-ED/SBA-15 (0.14 mmol/$g_{SiO2}$) and Ph-6-PD/SBA-15 (0.28 mmol/$g_{SiO2}$) over 25 consecutive cycles. Adsorption was performed at 35° C. and 400 ppm $CO_2$/He for 1 h, while desorption was performed in UHP He at 90° C. for 10 min. Note: Plots of the measured $CO_2$ capacity during temperature-swing cycles for Ph-X-YY/SBA-15 are shown in FIG. 12.
FIGS. 5A-5B illustrate the weight change (%) recorded during 24 h exposure of 21% $O_2$/He to 50% Ph-3-ED/SBA-15 and 50% Ph-3-PD/SBA-15 sorbents at (FIG. 5A) 90° C.
Figures 12A, 12B, 12C, 12D:
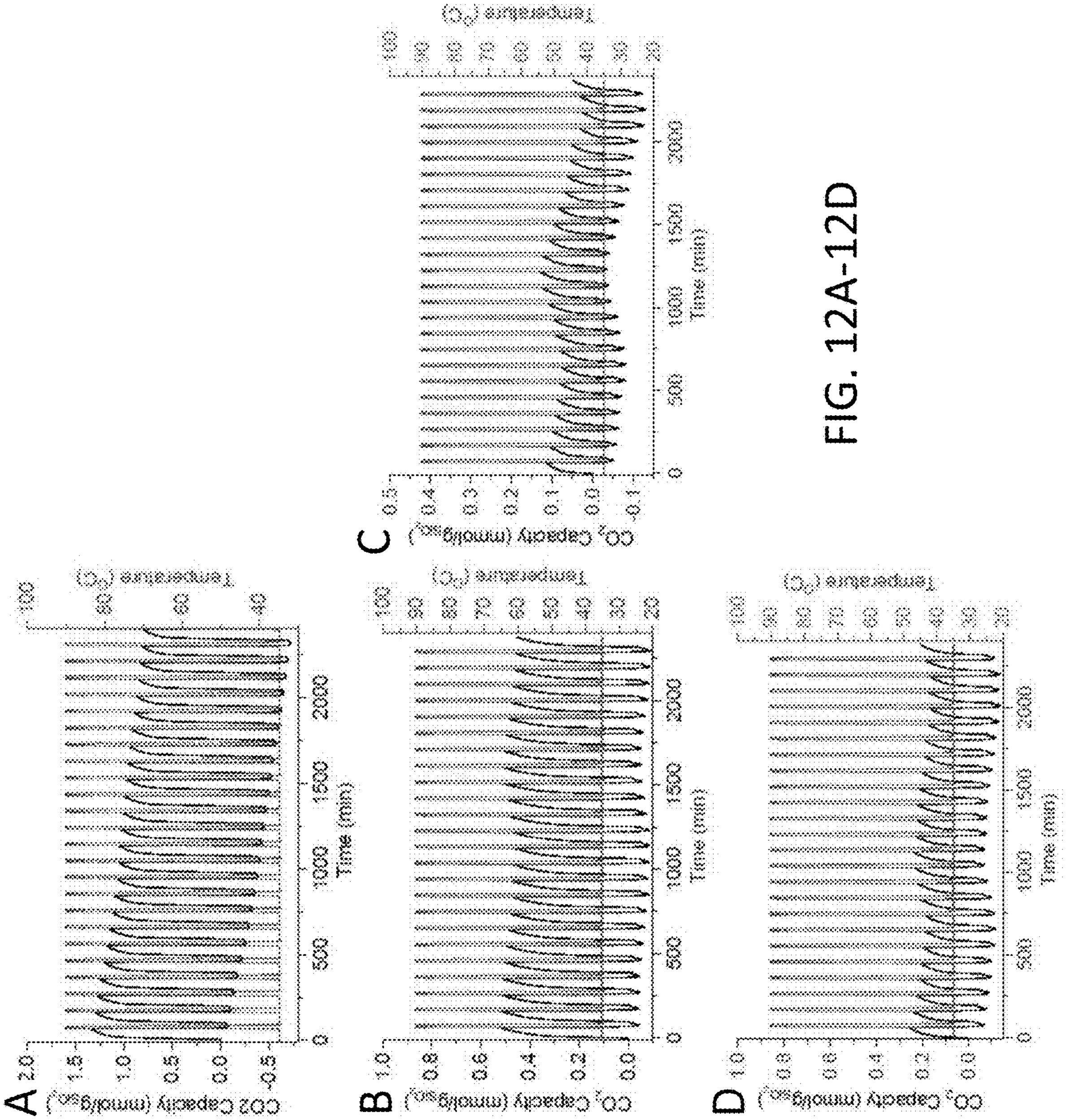
FIGS. 12A-12D illustrate $CO_2$ temperature-swing cycles for the (FIG. 12A) 50% Ph-3-ED/SBA-15 (FIG. 12B) 50% Ph-3-PD/SBA-15, (FIG. 12C) 50% Ph-6-ED/SBA-15 and (FIG. 12D) 50% Ph-6-PD/SBA-15. Adsorption was performed in 400 ppm $CO_2$/He at 35° C., desorption was performed in UHP He at 90° C. for 10 min. The number of cycles was 25.
Figures 13, 14:
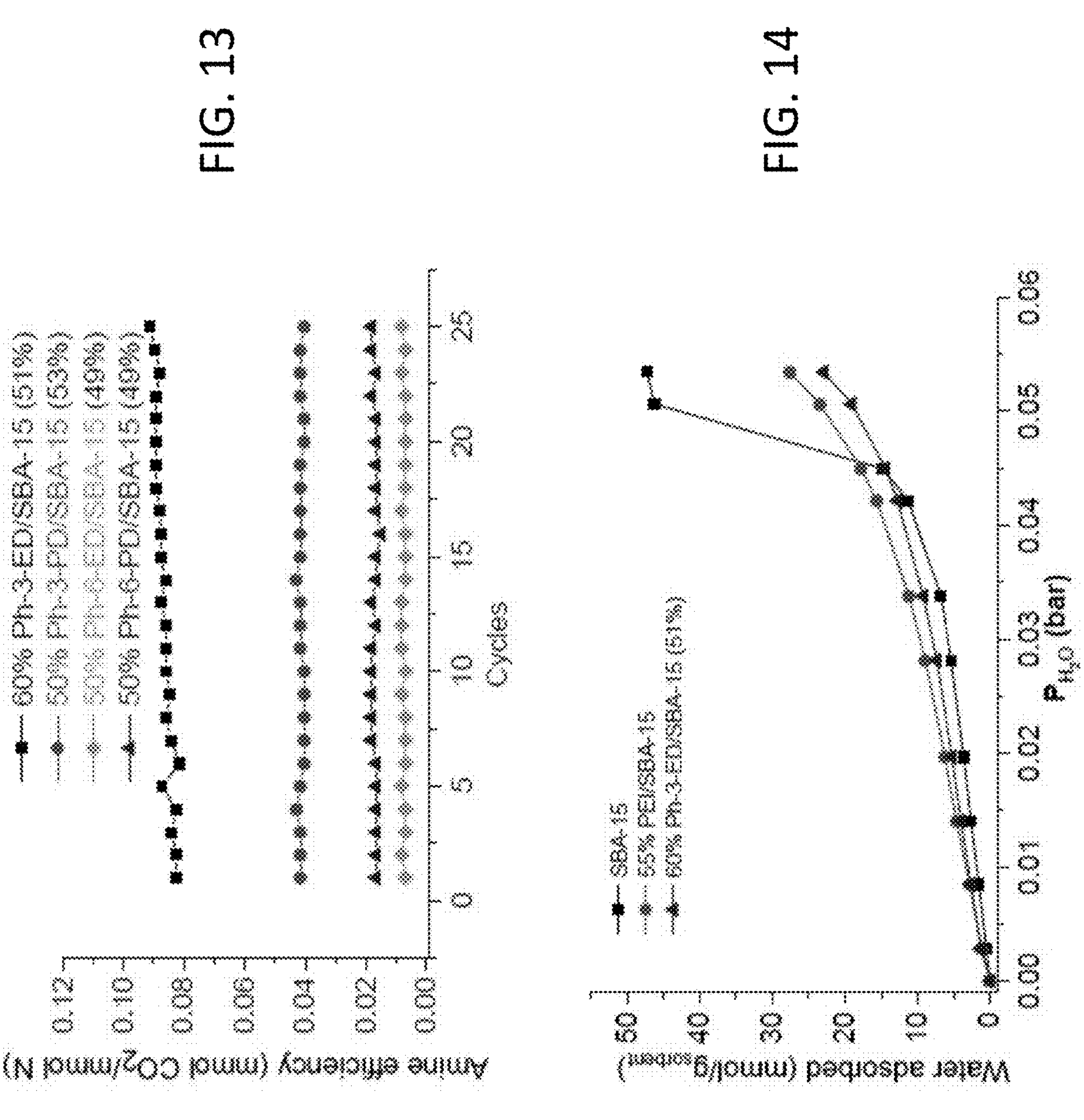
FIG. 13 illustrates amine efficiencies calculated from the temperature-swing cycles for Ph-3-ED/SBA-15, Ph-3-PD/SBA-15, Ph-6-ED/SBA-15 and Ph-6-PD/SBA-15 composites.
FIG. 14 illustrates the comparison of the water vapor adsorption isotherms for Ph-3-ED/SBA-15, PEI/SBA and SBA-15 at 35° C.

Temperature-swing cycles: To mimic the practical DAC working conditions, temperature-swing cycles of the Ph-X-YY/SBA-15 composite materials were assessed by using the high organic loading samples (~50%) as they displayed, in general, the highest $CO_2$ adsorption capacities. In the calculation of the $CO_2$ uptake (FIG. 4Aa), the sample mass recorded after the initial pretreatment at 110° C. for 2 h was subtracted from the mass in all subsequent cycles, allowing the direct plotting of the cyclic $CO_2$ uptake. By comparing the adsorption profiles recorded for 12 h for the 60% Ph-3-ED/SBA-15 sorbent (FIG. 3A) with the first 5-6 temperature-swing adsorption cycles recorded over 1 h at 35° C. (FIG. 4A), it can be concluded that approximately 70% of the 12 h pseudo equilibrium capacity was routinely reached within 1 h. For the last 12-15 cycles, this value slightly increased to about 75%. The baseline of the $CO_2$ capacity gradually shifts downwards due to a combined slow loss (1.5%) of water and possibly Ph-3-ED (FIG. 12A-12D). However, loss of Ph-3-ED from the sorbent does not affect the $CO_2$ capacity or amine efficiency of the sorbents (FIGS. 4B and 13). The similar phenomena was also observed in previous study with a linear PPI ($M_w$=1000 gm/mol)/SBA-15 sorbent.[55] A similar trend was observed for the 50% Ph-3-PD/SBA-15 adsorbent (FIG. 4B). We also note that the baseline can also show irregular variability (FIG. 12A-12D), which also suggests that instrumental drift may contribute to the observed variability. FIG. 4B shows a slight increasing trend in the adsorption capacity with increasing number of cycles for the 60% Ph-3-ED/SBA-15. It was hypothesized that a slight mass loss along with restructuring of Ph-3-ED molecules takes place inside the pores, especially at high temperatures (desorption step). These combined phenomena possibly contributed to an increased accessibility of active amines sites that eventually resulted in a modest increase in $CO_2$ capacity.

It is noteworthy that the Ph-6-YY-based composites had significantly different uptake behavior. The 50% Ph-6-ED/SBA-15 sample reached only 20% of the pseudo-equilibrium capacity after 1 h and this value was constant through all 25 cycles despite the somewhat 'undulating' pattern of the curve (FIG. 12B). After 1 h of exposure the 50% Ph-6-PD/SBA-15 sample reached about 45% of the $CO_2$ uptake value recorded after 12 h (FIG. 4B, FIG. 12C). All Ph-XX-YY/SBA-15 sorbents showed stable $CO_2$ capacities and amine efficiencies over 25 cycles of temperature-swing adsorption-desorption cycling (FIGS. 4 and 13). The fact that all samples displayed steady working capacities suggests that the sorbent Ph-X-YY molecules did not deactivate during the temperature-swing cycles. On the contrary, after each regeneration step (desorption of $CO_2$) performed at 90° C. for 10 min, the sorbent was still able to capture $CO_2$ at a constant rate. The original PEI-based adsorbents showed high $CO_2$ capacity for the 1st cycle but lost capacity significantly over temperature swing cycles in dry conditions, mostly due to degradation and/or leaching of amines.[2, 67-69] The stability of Ph-X-YY sorbents during temperature-swing-cycles enable their potential integration into practical DAC applications.

compared to linear and branched PEI-based sorbents.[11, 55-56] In addition to the physical effect of spacing the oligomeric alkyl amine chains differently, the aromatic cores can also alter the electronics of the amine molecules. The present data suggest that the phenyl core does not create structures where the ethyl or propyl spacers are significantly distinguished in oxidative stability, in contrast to our work on linear and dendritic small alkylamine molecules. Thus, it appears that the relative stability of ethyl vs. propyl linkers depend in part on their adjacent functional groups (i.e. alkyl vs. aryl species).

TABLE 1

$CO_2$ Capacity and Amine Efficiency Values Calculated after Accelerated Oxidation Conditions and Its Retained Performance.

| Composites | $CO_2$ capacity ($mmol/g_{SiO2}$) Before oxidation | After oxidation 90° C. | After oxidation 110° C. | Amine efficiency (mmol $CO_2$/mmol N) Before oxidation | After oxidation 90° C. | After oxidation 110° C. | Retained (%) $CO_2$ capacity/ Amine efficiency 90° C. | 110° C. |
|---|---|---|---|---|---|---|---|---|
| 50% Ph-3-ED/SBA-15 | 1.43 | 0.51 | 0.3 | 0.13 | 0.05 | 0.03 | 35/39 | 20/23 |
| 50% Ph-3-PD/SBA-15 | 1.23 | 0.27 | 0.15 | 0.1 | 0.02 | 0.01 | 22/20 | 13/10 |

Accelerated Oxidation Stability of the Ph-X-YY sorbents: To assess the oxidative stability of the composites, the best performing sorbents, Ph-3-YY/SBA-15, were exposed to an accelerated oxidative treatment at high temperatures (110° C. and 90° C.) in the presence of 02 (21%) for the duration of 24 h (FIG. 5). These experiments represent an accelerated exposure relevant to practical sorbent operation conditions that involve exposure to the oxygen-containing air at elevated temperatures, for example during process upsets.[11, 50, 55-56] FIG. 5 displays the normalized mass change of sorbents during the accelerated oxidation process at two different temperatures and adsorption of $CO_2$ (400 ppm/He) for 12 h at 35° C.

Treatment at a lower temperature of 90° C. was performed to be consistent with the desorption steps of a hypothetical temperature-swing process illustrated above in FIG. 4, whereas 110° C. gives a harsher exposure. The 50% Ph-3-ED/SBA-15 sorbent showed an initial abrupt mass loss, likely due to loss of physisorbed water and ambient $CO_2$ accumulated during sample storage. Later, additional mass was gradually lost at 90° C. (~2%) and 110° C. (4%). As listed in Table 1, the sample retained 35% of its initial $CO_2$ adsorption performance and 39% of its amine efficiency after treatment at 90° C. These numbers were a little smaller for the 110° C. oxidative treatments, 20% and 23%, respectively. After oxidation treatment at 90° C., the 50% Ph-3-ED/SBA-15 sample adsorbed a larger amount of $CO_2$ than when treated at 110° C. This trend was observed despite the fact that for the last ~30% of the oxidative treatment time, the change in sample mass was similar at the two treatment temperatures. In the case of the 50% Ph-3-PD/SBA-15 sample, the retained $CO_2$ capacity and amine efficiency were only ~20% (90° C.) and ~10% (90° C.) (Table 1). The above low retention values suggest that likely combined mass loss (evaporation) and oxidative degradation of some amine active sites occurred during accelerated oxidation treatments. This finding is contrary to results reported for linear and branched PPI-based sorbents that showed higher resistance to oxidative degradation of PPI based sorbents as Dry and Humid $CO_2$ Adsorption Capacity Measurement Using a Fixed Bed:

As DAC typically consists of capturing $CO_2$ in the presence of substantial amounts of humidity in the air, it is essential to evaluate the effect of humid conditions on the $CO_2$ adsorbent. Previously, it has been shown that under dry conditions, the interaction between $CO_2$ and amines leads to formation of carbamates with a $CO_2$/N ratio of 0.5. On the other hand, in presence of moisture, the interaction between $CO_2$ and amine can also result in the formation of bicarbonates with $CO_2$/N ratio of 1.[67, 70-71] For example, Wang et al. demonstrated that, the $CO_2$ adsorption capacity and the stability of the PEI ($M_w$=600) based adsorbent increased significantly in the presence of moisture. The adsorbent showed increases in $CO_2$ adsorption capacities by 21% and 15% for $CO_2$ concentrations of 5000 and 400 ppm, respectively, with 80% RH.[72] In the case of 400 ppm $CO_2$ adsorption, the amine efficiency was increased from 0.18 to 0.2 mmol $CO_2$/mmol N (~11%). Wang et al. suggest that the increase in $CO_2$ capacity for the 400 ppm condition is lower compared to the 5000 ppm due to competitive adsorption between $CO_2$ and $H_2O$ molecules.[72] In another example, aminopropyl-grafted pore-expanded MCM-41 silica (MONO-PE-MCM-41) was investigated under both humid and dry $CO_2$ (5% in $N_2$) conditions. Under dry conditions, the $CO_2$/N ratio was ~0.5 and with the increase in RH to 210% and 610% the adsorption capacity increased by 16% and 22%, respectively. The major increase in the $CO_2$/N ratio was observed at 74% RH, corresponding to a $CO_2$/N ratio of 0.78.[73] This appears consistent with NMR studies that required excess water to enable detection of bicarbonate species, with carbamate species dominating at lower humidity levels.[74] However, water vapor has also been reported to have a negative impact on low-concentration $CO_2$ capture on supported amine sorbents; water adsorbed in excess on the active amines sites can inhibit $CO_2$ adsorption and capacity.[75-76] These results suggest that RH can impact the $CO_2$ capacity in varied ways depending on the relative concentration of water vapor and $CO_2$. Regeneration of sorbents for $CO_2$ capture under high humidity conditions can also imply higher energy for regeneration if the water is removed from the sorbent in each cycle.[77-78]

Figure 6:
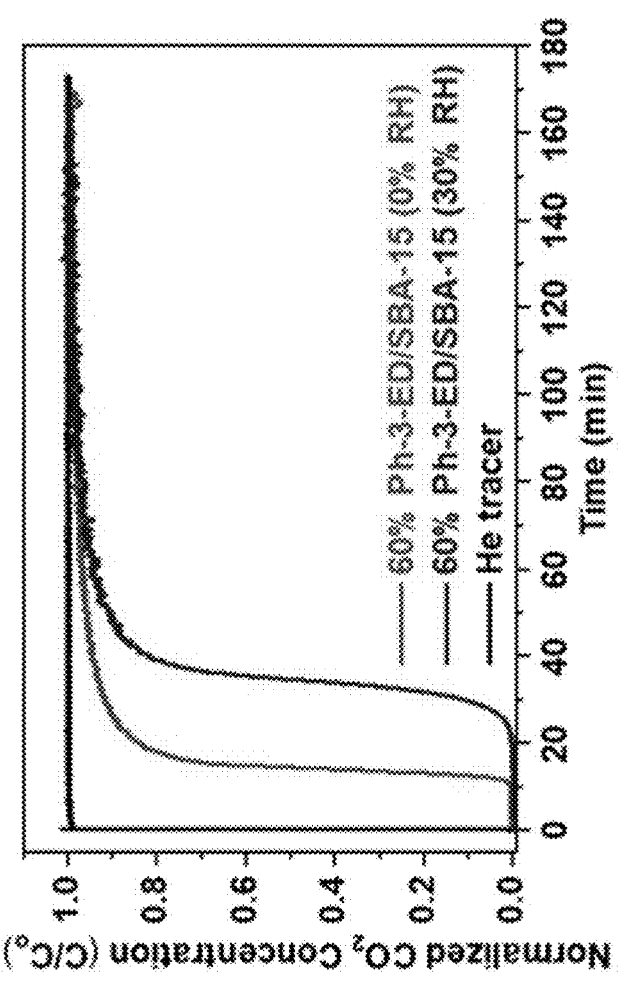
FIG. 6 illustrates breakthrough curves for the 60% Ph-3-ED/SBA-15 sorbent under dry and humid (30% RH) conditions. $CO_2$ adsorption conditions: 400 ppm $CO_2$/He, 90 mL/min flow rate, 35° C.
Figures 7A, 7B, 7C, 7D:
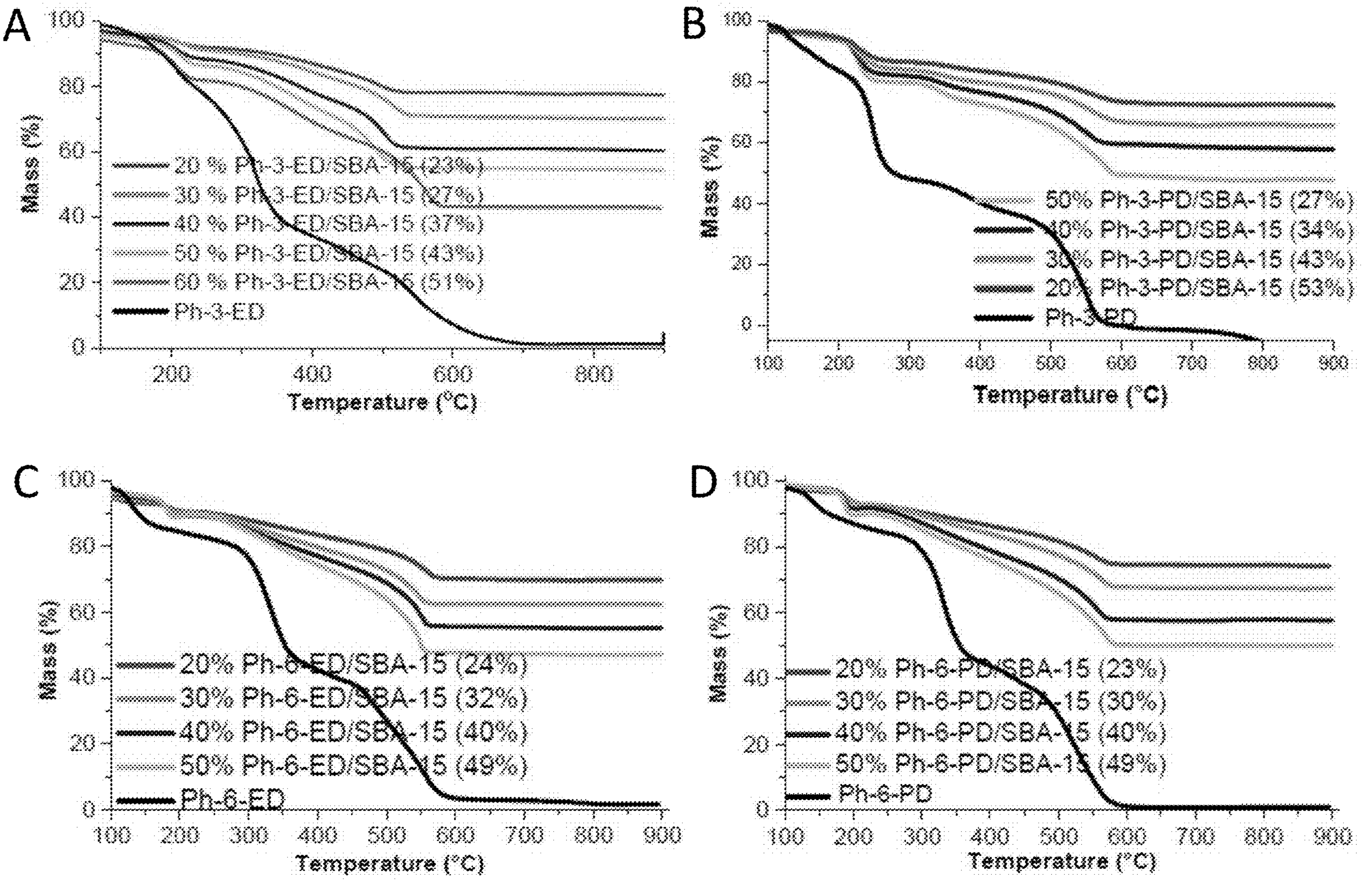
FIGS. 7A-7D illustrate TGA curves for (FIG. 7A) Ph-3-ED/SBA-15, (FIG. 7B) Ph-3-PD/SBA15, (FIG. 7C) Ph-6-ED/SBA-15 and (FIG. 7D) Ph-6-PD/SBA-15 composites with target and experimental various organic loading. Each graph contains the trace of the respective unsupported Ph-X-YY molecule.
Figure 8A:
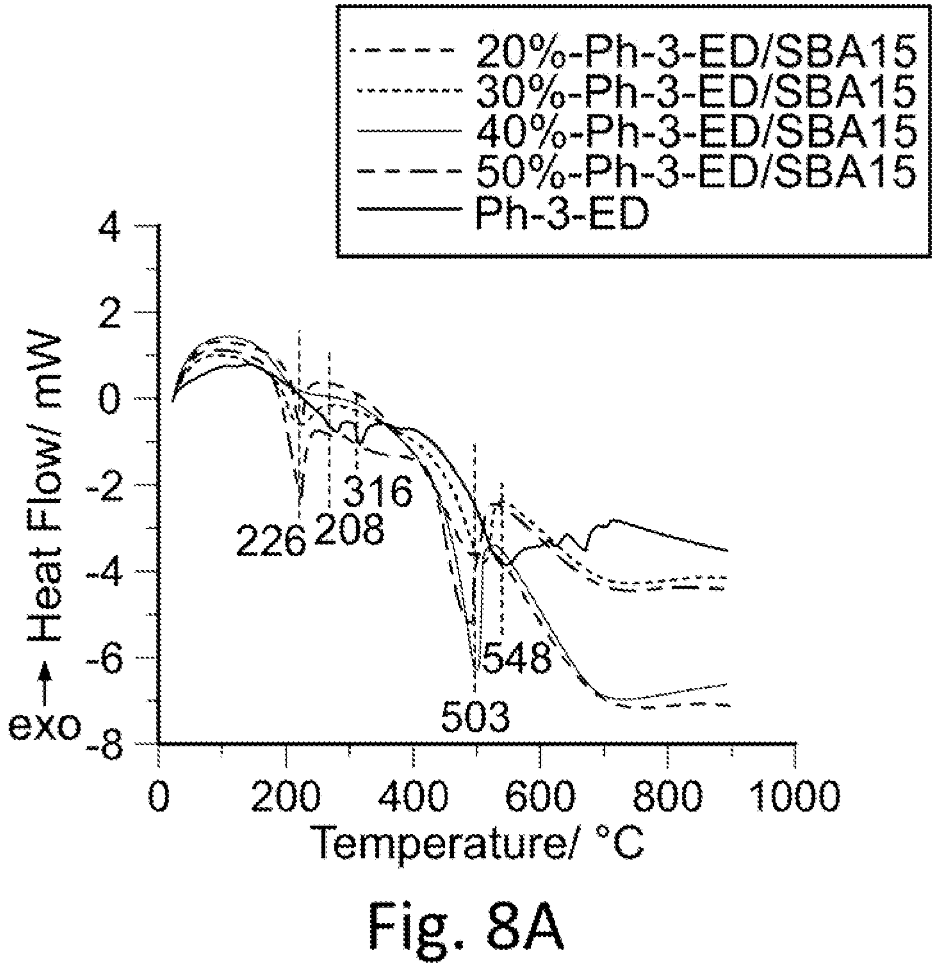
FIGS. 8A-8D illustrate differential scanning calorimetry profiles of (FIG. 8A) Ph-3-ED/SBA-15, (FIG. 8B) Ph-3-PD/SBA-15, (FIG. 8C) Ph-6-ED/SBA-15 and (FIG. 8D) Ph-6-PD/SBA-15 composites. Each graph contains the trace of the unsupported Ph-XX-YY.
Figure 8B:
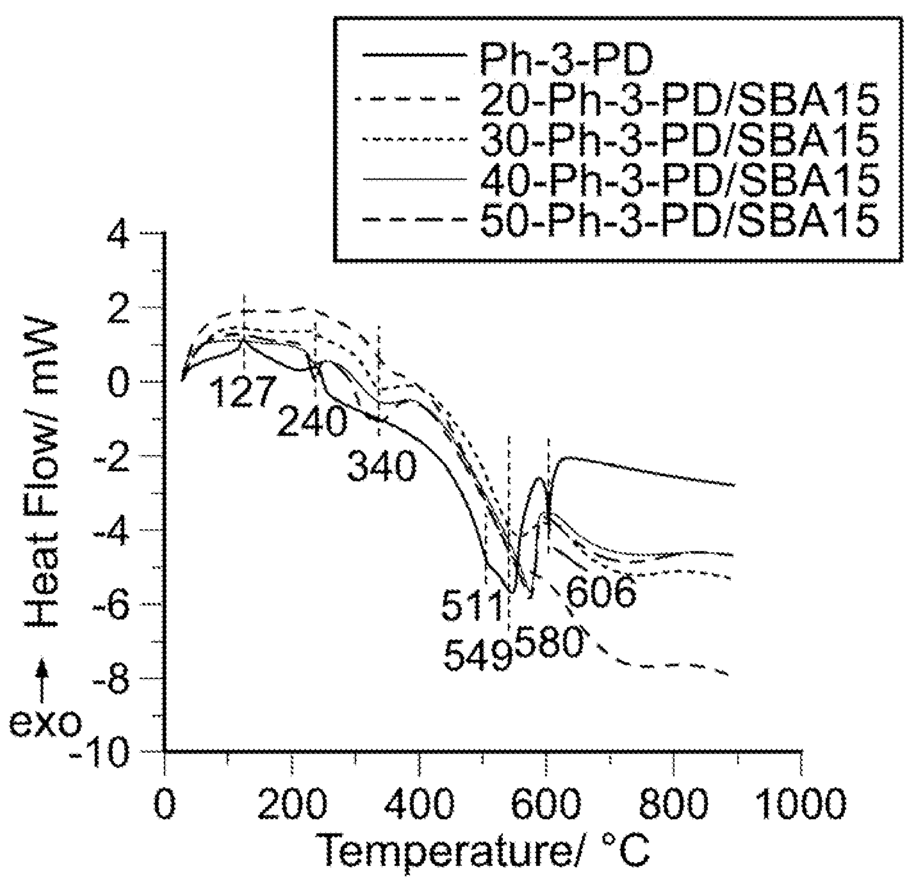
Figure 8C:
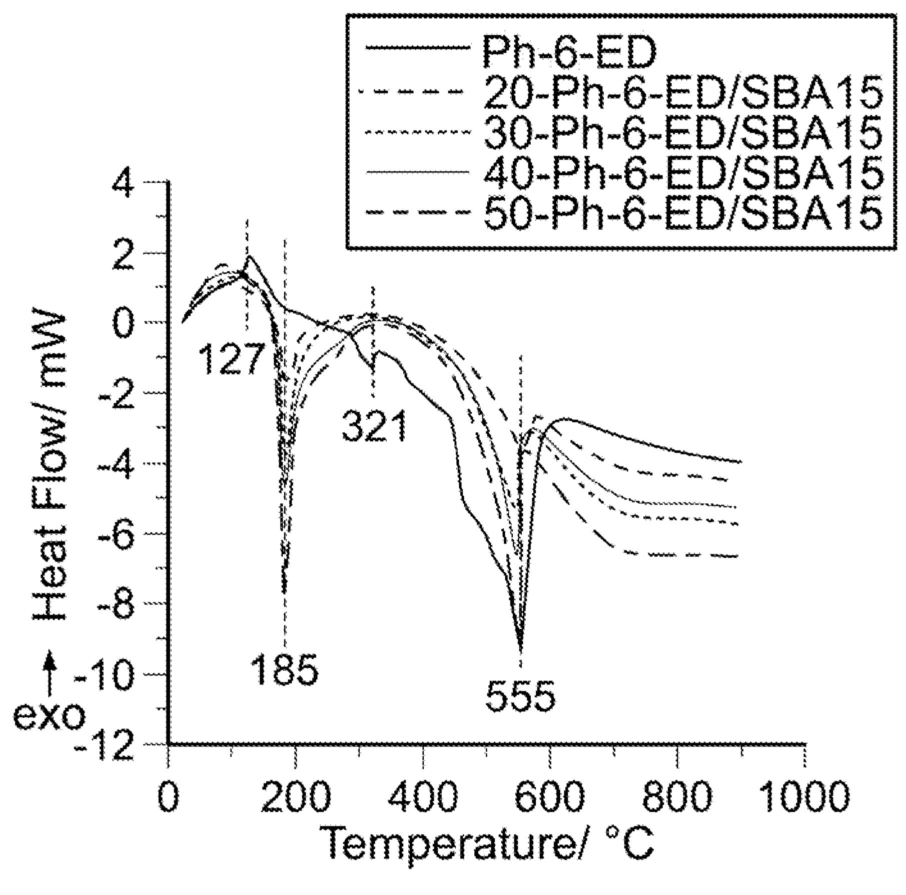
Figure 8D:
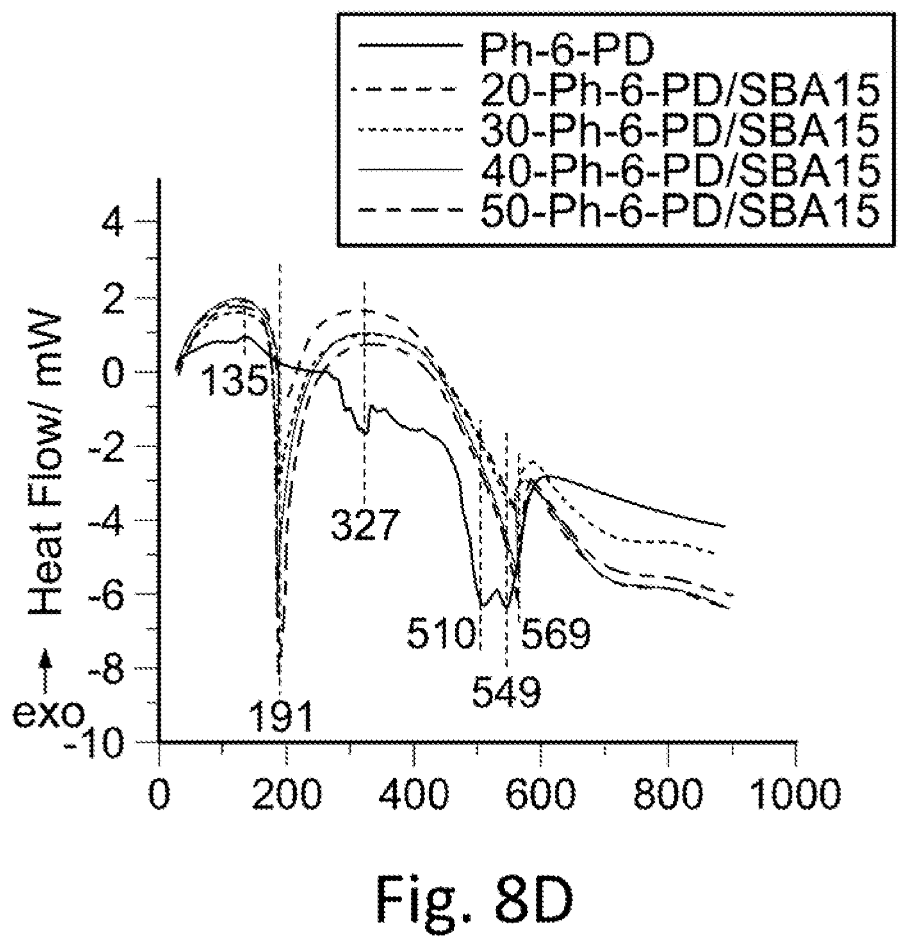
Figures 9A, 9B, 9C, 9D:
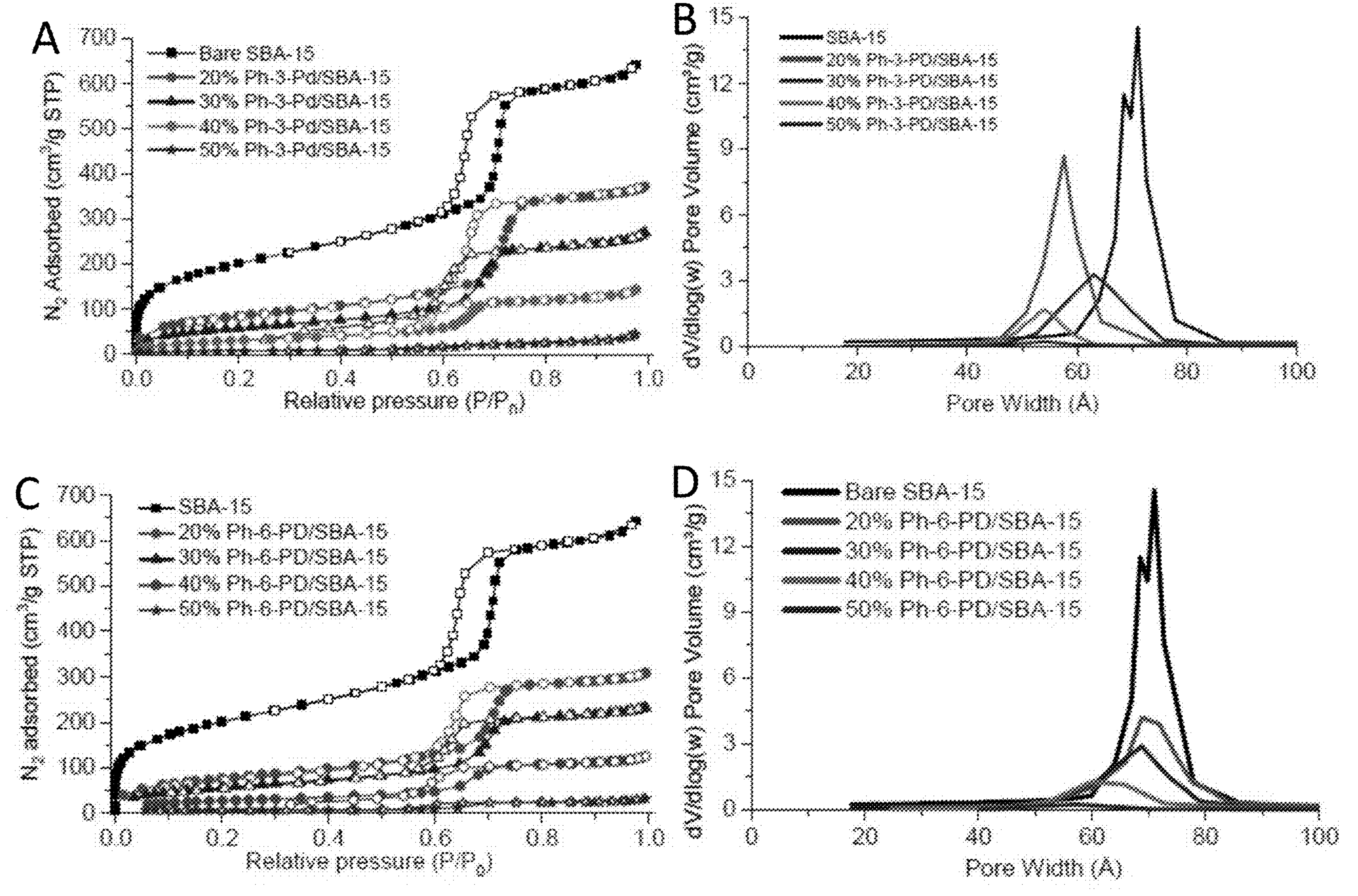
FIGS. 9A-9D illustrate nitrogen physisorption isotherms (FIG. 9A and FIG. 9C) and pore size distribution (FIG. 9B and FIG. 9D) for Ph-3-PD/SBA-15 (FIG. 9A and FIG. 9B), Ph-6-PD/SBA-15 (FIG. 9C and FIG. 9D) composites of various organic loadings (0-50%) recorded at 77K. Each graph contains the trace of bare SBA15.

The 60% Ph-3-ED/SBA-15 was investigated for the effect of relative humidity (30%) using an in-house constructed fixed bed system (35° C., 400 ppm $CO_2/N_2$). FIG. 6 shows that the $CO_2$ breakthrough time increases to 22 min in the presence of 30% RH at 35° C. The breakthrough capacity (2.73 mmol $CO_2/g_{SiO2}$) under humid conditions was ~3 times higher when compared to the breakthrough capacity under dry conditions (0.83 mmol $CO_2/g_{SiO2}$). The equilibrium $CO_2$ capacity increased by ~81% from 1.6 mmol/$g_{SiO2}$ to 2.9 mmol/$g_{SiO2}$ with 30% relative humidity. The amine efficiency of Ph-3-ED/SBA-15 was increased by 70%, from 0.1 to 0.17 $CO_2$/N using 400 ppm $CO_2$ with 30% RH (Table 2). However, although the increase in the amine efficiency for Ph-3-ED/SBA-15 under humid conditions is significant, the overall amine efficiency of the sorbent remains lower than some others in the literature, such as PEI/MC (0.2 mmol $CO_2$/mmol N) and MONO-PE-MCM-41 (0.78 mmol $CO_2$/mmol N) adsorbent.[72-73] The slope of the $CO_2$ breakthrough curve under humid conditions appeared to be almost identical to that of the breakthrough curve under dry conditions, suggesting a negligible effect of water vapor at 30% RH on the $CO_2$ sorption kinetics.

The $CO_2$ capacity obtained for dry 400 ppm $CO_2$ adsorption from the fixed bed system was 1.6 mmol/$g_{SiO2}$, which is similar to the $CO_2$ capacity obtained from TGA (1.9 mmol/$g_{SiO2}$). $CO_2$ from the dry feed mixture breaks through the bed after 10 min and approaches saturation at approximately 150 min (FIG. 6). The equilibrium capacities of both the dry and humid runs as shown in Table 2 were measured when the outlet $CO_2$ concentration was 99% of the inlet feed $CO_2$ concentration. The minor difference in the equilibrium $CO_2$ capacity of the 60% Ph-3-ED/SBA-15 sorbent under dry conditions from the fixed bed measurements and TGA measurements is likely due to differing fwo patterns and heat/mass transport rates in each system.

The dynamic water vapor sorption (DVS) isotherm of the 60% Ph-3-ED/SBA-15 sorbent is shown in FIG. 14, and it is compared to the benchmark material, branched PEI/SBA-15, at equivalent organic loading. Similar to bare SBA-15, the DVS isotherms for PEI- and Ph-3-ED supported on SBA-15 show a linear increase in water vapor uptake proportional to the water vapor partial pressure until ~0.045 bar. The reduced water vapor uptake at higher partial pressures compared to the uptake of bare SBA-15 is likely due to the pore filling effect of amine loaded SBA-15 observed in the $N_2$ physisorption data and is consistently seen in previous reports.[62] The selectivity of $CO_2/H_2O$ of 60% Ph-3-ED/SBA-15 under humid conditions is 0.31, as the water capacity at 30% RH is approximately 3 times (4.69 mmol/$g_{sorbent}$) higher than the $CO_2$ capacity (1.45 mmol/$g_{sorbent}$) at 35° C., given that water concentration at 30% RH (1.7%) is 43 times that of $CO_2$ concentration (0.04%) under DAC conditions.

TABLE 2

Comparison of $CO_2$ Capacity and Amine Efficiency of Ph-3-ED and PEI based sorbents using TGA and Fixed Bed Adsorption Methods. Fixed Bed $CO_2$ Capacity Obtained with 0% and 30% Relative Humidity.

| Sample [$CO_2$ adsorption method] | Relative Humidity (RH) (%) | Breakthrough $CO_2$ capacity (mmol/gSiO$_2$) | Equilibrium $CO_2$ Capacity (mmol/ gSiO$_2$) | Amine efficiency (mmol $CO_2$/ mmol N) |
|---|---|---|---|---|
| 60% Ph-3-ED/SBA-15 [Fixed bed] | 0 | 0.83 | 1.6 | 0.1 |
| | 30 | 2.73 | 2.9 | 0.17 |
| 60% Ph-3-ED/SBA-15 [TGA] | 0 | — | 1.9 | 0.11 |
| 60% PEI/Mesoporous Carbon [Fixed bed][A] | 0 | — | 2.25 | 0.18 |
| | 80 | — | 2.58 | 0.2 |

[A]The $CO_2$ capacity and amine efficiency of 60% PEI (600)/mesoporous carbon are adopted from Wang et al. (adsoption conditions: 25° C., 400 ppm $CO_2/N_2$, flow rate of 50 mL/min, RH = 80%).[72]

Conclusions:

Polyamine molecules based on alkyl diamine-substituted aryl cores (Ph-X-YY) were prepared by nucleophilic substitution using a one-pot synthesis in high yield. Subsequently, these amine rich molecules were impregnated into a mesoporous silica substrate (SBA-15) with predetermined organic loadings. The organic loadings of the resultant composite materials were confirmed by TGA and elemental analysis. The BET surface area and total pore volume of the Ph-X-YY/solid substrate composites were assessed by $N_2$ physisorption. A decrease in BET surface area and total pore volume of SBA-15 was observed with an increase in Ph-X-YY loading into the pores. Ph-6-YY shows comparatively higher pore filling as compared to Ph-3-YY at the same organic loadings, mostly attributed to the bulkiness and steric effects of molecules as a result of a higher number of ring substitutions. The adsorbents with the 3-diamine substitution aryl core (Ph-3-YY) showed overall higher $CO_2$ capacity and amine efficiency. Diamines with ethyl spacers (Ph-X-ED) showed higher $CO_2$ capacities and amine efficiencies as compared to propyl spacers (Ph-X-PD). This study further revealed that the number of substitutions on the aryl core impacts the $CO_2$ capacity. The reduced $CO_2$ uptake of the Ph-6-YY based sorbents as compared to Ph-3-YY/SBA-15 sorbents was likely due to the bulky molecular architecture of the Ph-6-YY that results in poor $CO_2$ diffusion to active amines. Given the characteristics of each amine molecule, a maximum dry $CO_2$ capacity of 1.9 mmol/$g_{SiO2}$ was obtained using the Ph-3-ED/SBA-15 sorbent.

Temperature-swing adsorption-desorption cycles demonstrated a stable working capacity for these sorbents without any loss in $CO_2$ capacity and amine efficiency. This indicates no significant deactivation or volatilization of alkyl-aryl amine-rich molecules in the DAC process for the duration of the experiments. However, when subjected to accelerated oxidative treatment at 110° C., the $CO_2$ capacity of 50% Ph-3-ED/SBA-15 and 50% Ph-6-PD/SBA-15 decreased to 22% and 10% of their initial values, respectively. Similar maximum $CO_2$ capacities were obtained for 60% Ph-3-ED/SBA-15 from TGA and fixed bed methods under dry conditions. $CO_2$ adsorption under humid conditions with 30% relative humidity showed a significant, three-fold enhancement in the breakthrough $CO_2$ capacity and a two-fold increase in the breakthrough time as compared to dry conditions in the fixed bed contactor. The collected results demonstrate the potential for using alkyl-aryl amine-rich molecules in sorbents for $CO_2$ capture. This study also offers a completely different set of amine rich sorbent structures vs. the traditional linear and branched family of PEI based sorbents.

REFERENCES FOR EXAMPLE 1

1. National Academies of Sciences, E.; Medicine, Negative Emissions Technologies and Reliable Sequestration: A Research Agenda. The National Academies Press: Washington, D.C., 2019; p 510. https://www.ncbi.nlm.nih.gov/books/NBK541442/
2. Sanz-Pérez, E. S.; Murdock, C. R.; Didas, S. A.; Jones, C. W., Direct Capture of $CO_2$ from Ambient Air. *Chem. Rev.* 2016, 116 (19), 11840-11876. https://doi.org/10.1021/acs.chemrev.6b00173
3. Brethomé, F. M.; Williams, N. J.; Seipp, C. A.; Kidder, M. K.; Custelcean, R., Direct air capture of $CO_2$ via aqueous-phase absorption and crystalline-phase release using concentrated solar power. *Nat. Energy* 2018, 3 (7), 553-559. https://doi.org/10.1038/s41560-018-0150-z
4. Shi, X.; Xiao, H.; Azarabadi, H.; Song, J.; Wu, X.; Chen, X.; Lackner, K. S., Sorbents for Direct Capture of $CO_2$ from Ambient Air. *Angew. Chem. Int. Ed.* 2020, 59, 2-25. https://doi.org/10.1002/anie.201906756
5. Choi, S.; Drese, J. H.; Eisenberger, P. M.; Jones, C. W., Application of Amine-Tethered Solid Sorbents for Direct $CO_2$ Capture from the Ambient Air. *Environ. Sci. Technol.* 2011, 45 (6), 2420-2427. https://doi.org/10.1021/es102797w
6. Xu, X.; Myers, M. B.; Versteeg, F. G.; Pejcic, B.; Heath, C.; Wood, C. D., Direct air capture (DAC) of $CO_2$ using polyethylenimine (PEI) "snow": a scalable strategy. *Chem. Commun.* 2020. https://doi.org/10.1039/D0CC02572K
7. Breyer, C.; Fasihi, M.; Bajamundi, C.; Creutzig, F., Direct Air Capture of $CO_2$: A Key Technology for Ambitious Climate Change Mitigation. *Joule* 2019, 3 (9), 2053-2057. https://doi.org/10.1016/j.joule.2019.08.010
8. Keith, D. W.; Holmes, G.; St. Angelo, D.; Heidel, K., A Process for Capturing $CO_2$ from the Atmosphere. *Joule* 2018, 2 (8), 1573-1594. https://doi.org/10.1016/j.joule.2018.05.006
9. Wurzbacher, J. A.; Gebald, C.; Steinfeld, A., Separation of $CO_2$ from air by temperature-vacuum swing adsorption using diamine-functionalized silica gel. *Energy Environ. Sci.* 2011, 4 (9), 3584-3592. https://doi.org/10.1039/C1EE01681D
10. Xu, X.; Song, C.; Andresen, J. M.; Miller, B. G.; Scaroni, A. W., Novel Polyethylenimine-Modified Mesoporous Molecular Sieve of MCM-41 Type as High-Capacity Adsorbent for $CO_2$ Capture. *Energy & Fuels* 2002, 16 (6), 1463-1469. https://doi.org/10.1021/ef020058u
11. Pang, S. H.; Lee, L.-C.; Sakwa-Novak, M. A.; Lively, R. P.; Jones, C. W., Design of Aminopolymer Structure to Enhance Performance and Stability of $CO_2$ Sorbents: Poly(propylenimine) vs Poly(ethylenimine). *J. Am. Chem. Soc.* 2017, 139 (10), 3627-3630. https://doi.org/10.1021/jacs.7b00235
12. Belmabkhout, Y.; Serna-Guerrero, R.; Sayari, A., Amine-bearing mesoporous silica for $CO_2$ removal from dry and humid air. *Chem. Eng. Sci.* 2010, 65 (11), 3695-3698. https://doi.org/10.1016/j.ces.2010.02.044
13. Stuckert, N. R.; Yang, R. T., $CO_2$ Capture from the Atmosphere and Simultaneous Concentration Using Zeolites and Amine-Grafted SBA-15. *Environ. Sci. Technol.* 2011, 45 (23), 10257-10264. https://doi.org/10.1021/es202647a
14. Bali, S.; Leisen, J.; Foo, G. S.; Sievers, C.; Jones, C. W., Aminosilanes Grafted to Basic Alumina as $CO_2$ Adsorbents—Role of Grafting Conditions on $CO_2$ Adsorption Properties. *ChemSusChem* 2014, 7 (11), 3145-3156. https://doi.org/10.1002/cssc.201402373
15. Kolle, J. M.; Sayari, A., Covalently Immobilized Polyethylenimine for $CO_2$ Adsorption. *Ind. Eng. Chem. Res.* 2020, 59 (15), 6944-6950. https://doi.org/10.1021/acs.iecr.9b04669
16. Park, S. J.; Lee, J. J.; Hoyt, C. B.; Kumar, D. R.; Jones, C. W., Silica supported poly(propylene guanidine) as a $CO_2$ sorbent in simulated flue gas and direct air capture. *Adsorption* 2019, 26, 89-101. https://doi.org/10.1007/s10450-019-00171-w
17. Choi, S.; Gray, M. L.; Jones, C. W., Amine-Tethered Solid Adsorbents Coupling High Adsorption Capacity and Regenerability for $CO_2$ Capture From Ambient Air. *ChemSusChem* 2011, 4 (5), 628-635. https://doi.org/10.1002/cssc.201000355
18. Heydari-Gorji, A.; Sayari, A., Thermal, Oxidative, and $CO_2$—Induced Degradation of Supported Polyethylenimine Adsorbents. *Ind. Eng. Chem. Res.* 2012, 51 (19), 6887-6894. https://doi.org/10.1021/ie3003446
19. Nakao, S.-i.; Yogo, K.; Goto, K.; Kai, T.; Yamada, H., $CO_2$ Capture with Adsorbents. In *Advanced $CO_2$ Capture Technologies: Absorption, Adsorption, and Membrane Separation Methods*, Springer International Publishing: Chain, 2019; pp 45-63. https://www.springer.com/gp/book/9783030188573
20. Sandhu, N. K.; Pudasainee, D.; Sarkar, P.; Gupta, R., Steam Regeneration of Polyethylenimine-Impregnated Silica Sorbent for Postcombustion $CO_2$ Capture: A Multicyclic Study. *Ind. Eng. Chem. Res.* 2016, 55 (7), 2210-2220. https://doi.org/10.1021/acs.iecr.5b04741
21. Chaikittisilp, W.; Lunn, J. D.; Shantz, D. F.; Jones, C. W., Poly(L-lysine) Brush-Mesoporous Silica Hybrid Material as a Biomolecule-Based Adsorbent for $CO_2$ Capture from Simulated Flue Gas and Air. *Chem. Eur. J.* 2011, 17 (38), 10556-10561. https://doi.org/10.1002/chem.201101480
22. Hicks, J. C.; Drese, J. H.; Fauth, D. J.; Gray, M. L.; Qi, G.; Jones, C. W., Designing Adsorbents for $CO_2$ Capture from Flue Gas-Hyperbranched Aminosilicas Capable of Capturing CO2 Reversibly. *J. Am. Chem. Soc.* 2008, 130 (10), 2902-2903. https://doi.org/10.1021/ja077795v
23. Yoo, C.-J.; Narayanan, P.; Jones, C. W., Self-supported branched poly(ethyleneimine) materials for $CO_2$ adsorption from simulated flue gas. *J. Mater. Chem.* A 2019, 7 (33), 19513-19521. https://doi.org/10.1039/C9TA04662C
24. Liu, F.-Q.; Wang, L.-L.; Li, G.-H.; Li, W.; Li, C.-Q., Hierarchically Structured Graphene Coupled Microporous Organic Polymers for Superior $CO_2$ Capture. *ACS Appl. Mater. Interfaces* 2017, 9 (39), 33997-34004. https://doi.org/10.1021/acsami.7b11492
25. Sun, L.-B.; Kang, Y.-H.; Shi, Y.-Q.; Jiang, Y.; Liu, X.-Q., Highly Selective Capture of the Greenhouse Gas $CO_2$ in Polymers. *ACS Sustainable Chem. Eng.* 2015, 3 (12), 3077-3085. https://doi.org/10.1021/acssuschemeng.5b00544
26. Sun, L.-B.; Li, A.-G.; Liu, X.-D.; Liu, X.-Q.; Feng, D.; Lu, W.; Yuan, D.; Zhou, H.-C., Facile fabrication of cost-effective porous polymer networks for highly selective $CO_2$ capture. *J. Mater. Chem.* A 2015, 3 (7), 3252-3256. https://doi.org/10.1039/C4TA06039C 27. Looper, R. W., D.; Jeyapalina, S.; Haussener, T.; Sebahar, P. R.; Reddy Hariprasada, R. K., Compositions and methods comprising a biocidal polyamine. U.S. Patent, US 20150038512 A1, Sep. 13, 2016
28. Looper, R. W., D.; Jeyapalina, S.; Haussener, T.; Sebahar, P. R.; Reddy Hariprasada, R. K., Methods of use for Compositions Comprising a Biocidal Polyamine. U.S. Patent, US 20140350017 A1, Nov. 27, 2014
29. Sawicki, M.; Lecerced, D.; Grillon, G.; Le Gall, B.; Sdrandour, A.-L.; Poncy, J.-L.; Bailly, T.; Burgada, R.; Lecouvey, M.; Challeix, V.; Leydier, A.; Pellet-Rostaing, S.; Ansoborlo, E.; Taran, F., Bisphosphonate sequestering agents. Synthesis and preliminary evaluation for in vitro and in vivo uranium(VI) chelation. *Eur. J Med. Chem.* 2008, 43 (12), 2768-2777. https://doi.org/10.1016/j.ejmech.2008.01.018
30. Bollini, P.; Choi, S.; Drese, J. H.; Jones, C. W., Oxidative Degradation of Aminosilica Adsorbents Relevant to Post-combustion $CO_2$ Capture. *Energy & Fuels* 2011, 25 (5), 2416-2425. https://doi.org/10.1021/ef200l40z
31. Kwon, H. T.; Sakwa-Novak, M. A.; Pang, S. H.; Sujan, A. R.; Ping, E. W.; Jones, C. W., Aminopolymer-Impregnated Hierarchical Silica Structures: Unexpected Equivalent $CO_2$ Uptake under Simulated Air Capture and Flue Gas Capture Conditions. *Chem. Mater.* 2019, 31 (14), 5229-5237. https://doi.org/10.1021/acs.chemmater.9b01474
32. Kong, W.; Liu, J., Ordered mesoporous carbon with enhanced porosity to support organic amines: efficient nanocomposites for the selective capture of $CO_2$. *New J. Chem.* 2019, 43 (15), 6040-6047. https://doi.org/10.1039/C9NJ00617F
33. Estevez, L.; Barpaga, D.; Zheng, J.; Sabale, S.; Patel, R. L.; Zhang, J.-G.; McGrail, B. P.; Motkuri, R. K., Hierarchically Porous Carbon Materials for $CO_2$ Capture: The Role of Pore Structure. *Ind. Eng. Chem. Res.* 2018, 57 (4), 1262-1268. https://doi.org/10.1021/acs.iecr.7b03879
34. Wang, X.; Ma, X.; Schwartz, V.; Clark, J. C.; Overbury, S. H.; Zhao, S.; Xu, X.; Song, C., A solid molecular basket sorbent for $CO_2$ capture from gas streams with low $CO_2$ concentration under ambient conditions. *Phys. Chem. Chem. Phys.* 2012, 14 (4), 1485-1492. https://doi.org/10.1039/C1CP23366A
35. Chaikittisilp, W.; Kim, H.-J.; Jones, C. W., Mesoporous Alumina-Supported Amines as Potential Steam-Stable Adsorbents for Capturing $CO_2$ from Simulated Flue Gas and Ambient Air. *Energy & Fuels* 2011, 25 (11), 5528-5537. https://doi.org/10.1021/ef201224v
36. Liu, Y.; Sajjadi, B.; Chen, W.-Y.; Chatterjee, R., Ultrasound-assisted amine functionalized graphene oxide for enhanced $CO_2$ adsorption. *Fuel* 2019, 247, 10-18. https://doi.org/10.1016/j.fuel.2019.03.011
37. Deng, J.; Liu, Z.; Du, Z.; Zou, W.; Zhang, C., Fabrication of PEI-grafted porous polymer foam for $CO_2$ capture. *J. Appl. Polym. Sci.* 2019, 136 (32), 47844. https://doi.org/10.1002/app.47844
38. Sevilla, M.; Fuertes, A. B., Sustainable porous carbons with a superior performance for $CO_2$ capture. *Energy Environ. Sci.* 2011, 4 (5), 1765-1771. https://doi.org/10.1039/COEE00784F
39. Hu, Z.; Wang, Y.; Shah, B. B.; Zhao, D., $CO_2$ Capture in Metal-Organic Framework Adsorbents: An Engineering Perspective. *Adv. Sustainable Syst.* 2019, 3 (1), 1800080. https://doi.org/10.1002/adsu.201800080
40. Hussain, A.; Farrukh, S.; Hussain, A.; Ayoub, M., Carbon capture from natural gas using multi-walled CNTs based mixed matrix membranes. *Environ. Technol.* 2019, 40 (7), 843-854. https://doi.org/10.1080/09593330.2017.1408696
41. Samanta, A.; Zhao, A.; Shimizu, G. K. H.; Sarkar, P.; Gupta, R., Post-Combustion $CO_2$ Capture Using Solid Sorbents: A Review. *Ind. Eng. Chem. Res.* 2012, 51 (4), 1438-1463. https://doi.org/10.1021/ie200686q
42. D'Alessandro, D. M.; Smit, B.; Long, J. R., Carbon Dioxide Capture: Prospects for New Materials. *Angew. Chem. Int. Ed.* 2010, 49 (35), 6058-6082. https://doi.org/10.1002/anie.201000431
43. Kumar, A.; Madden, D. G.; Lusi, M.; Chen, K.-J.; Daniels, E. A.; Curtin, T.; Perry IV, J. J.; Zaworotko, M. J., Direct Air Capture of $CO_2$ by Physisorbent Materials. *Angew. Chem. Int. Ed.* 2015, 54 (48), 14372-14377. https://doi.org/10.1002/anie.201506952
44. Seipp, C. A.; Williams, N. J.; Kidder, M. K.; Custelcean, R., $CO_2$ Capture from Ambient Air by Crystallization with a Guanidine Sorbent. *Angew. Chem. Int. Ed.* 2017, 56 (4), 1042-1045. https://doi.org/10.1002/ange.201610916
45. Lu, W.; Sculley, J. P.; Yuan, D.; Krishna, R.; Wei, Z.; Zhou, H.-C., Polyamine-Tethered Porous Polymer Networks for Carbon Dioxide Capture from Flue Gas. *Angew. Chem. Int. Ed.* 2012, 51 (30), 7480-7484. https://doi.org/10.1002/ange.201202176
46. Lu, W.; Sculley, J. P.; Yuan, D.; Krishna, R.; Zhou, H.-C., Carbon Dioxide Capture from Air Using Amine-Grafted Porous Polymer Networks. *J Phys. Chem. C* 2013, 117 (8), 4057-4061. https://doi.org/10.1021/jp311512q
47. Gelles, T.; Lawson, S.; Rownaghi, A. A.; Rezaei, F., Recent advances in development of amine functionalized adsorbents for $CO_2$ capture. *Adsorption* 2020, 26 (1), 5-50. https://doi.org/10.1007/s10450-019-00151-0
48. Zhang, W.; Sun, C.; Snape, C. E.; Sun, X.; Liu, H., Cyclic performance evaluation of a polyethylenimine/silica adsorbent with steam regeneration using simulated NGCC flue gas and actual flue gas of a gas-fired boiler in a bubbling fluidized bed reactor. *Int. J. Greenh. Gas Con.* 2020, 95, 102975. https://doi.org/10.1016/J.ijggc.2020.102975
49. Li, K.; Jiang, J.; Yan, F.; Tian, S.; Chen, X., The influence of polyethyleneimine type and molecular weight on the $CO_2$ capture performance of PEI-nano silica adsorbents. *Appl. Energy* 2014, 136, 750-755. https://doi.org/10.1016/j.apenergy.2014.09.057
50. Min, K.; Choi, W.; Kim, C.; Choi, M., Oxidation-stable amine-containing adsorbents for carbon dioxide capture. *Nat. Commun.* 2018, 9 (1), 726. https://doi.org/10.1038/s41467-018-03123-0
51. Goeppert, A.; Zhang, H.; Sen, R.; Dang, H.; Prakash, G. K. S., Oxidation-Resistant, Cost-Effective Epoxide-Modified Polyamine Adsorbents for $CO_2$ Capture from Various Sources Including Air. *ChemSusChem* 2019, 12 (8), 1712-1723. https://doi.org/10.1002/cssc.201802978
52. Guo, M.; Liang, S.; Liu, J.; Jin, J.; Mi, J., Epoxide-Functionalization of Grafted Tetraethylenepentamine on the Framework of an Acrylate Copolymer as a $CO_2$ Sorbent with Long Cycle Stability. *ACS Sustainable Chem. Eng.* 2020, 8 (9), 3853-3864. https://doi.org/10.1021/acssuschemeng.9b07318
53. Bali, S.; Chen, T. T.; Chaikittisilp, W.; Jones, C. W., Oxidative Stability of Amino Polymer-Alumina Hybrid Adsorbents for Carbon Dioxide Capture. *Energy & Fuels* 2013, 27 (3), 1547-1554. https://doi.org/10.1021/ef4001067
54. Wang, D.; Wang, X.; Song, C., Comparative Study of Molecular Basket Sorbents Consisting of Polyallylamine and Polyethylenimine Functionalized SBA-15 for $CO_2$ Capture from Flue Gas. *ChemPhysChem* 2017, 18 (22), 3163-3173. https://doi.org/10.1002/cphc.201700828

55. Pang, S. H.; Lively, R. P.; Jones, C. W., Oxidatively-Stable Linear Poly(propylenimine)-Containing Adsorbents for $CO_2$ Capture from Ultradilute Streams. *ChemSusChem* 2018, 11 (15), 2628-2637. https://doi.org/10.1002/cssc.201800438
56. Sarazen, M. L.; Sakwa-Novak, M. A.; Ping, E. W.; Jones, C. W., Effect of Different Acid Initiators on Branched Poly(propylenimine) Synthesis and $CO_2$ Sorption Performance. *ACS Sustainable Chem. Eng.* 2019, 7 (7), 7338-7345. https://doi.org/10.1021/acssuschemeng.9b00512
57. Sarazen, M. L.; Jones, C. W., Insights into Azetidine Polymerization for the Preparation of Poly(propylenimine)-Based $CO_2$ Adsorbents. *Macromolecules* 2017, 50 (23), 9135-9143. https://doi.org/10.1021/acs.macromol.7b02402
58. Linneen, N. N.; Pfeffer, R.; Lin, Y. S., Amine Distribution and Carbon Dioxide Sorption Performance of Amine Coated Silica Aerogel Sorbents: Effect of Synthesis Methods. *Ind. Eng. Chem. Res.* 2013, 52 (41), 14671-14679. https://doi.org/10.1021/ie401559u
59. Jahandar Lashaki, M.; Khiavi, S.; Sayari, A., Stability of amine-functionalized $CO_2$ adsorbents: a multifaceted puzzle. *Chem. Soc. Rev.* 2019, 48 (12), 3320-3405. https://doi.org/10.1039/C8CS00877A
60. Zhang, G.; Zhao, P.; Xu, Y.; Yang, Z.; Cheng, H.; Zhang, Y., Structure Property—$CO_2$ Capture Performance Relations of Amine-Functionalized Porous Silica Composite Adsorbents. *ACS Appl. Mater. Interfaces* 2018, 10 (40), 34340-34354. https://doi.org/10.1021/acsami.8b13069
61. Holewinski, A.; Sakwa-Novak, M. A.; Jones, C. W., Linking $CO_2$ Sorption Performance to Polymer Morphology in Aminopolymer/Silica Composites through Neutron Scattering. *J. Am. Chem. Soc.* 2015, 137 (36), 11749-11759. https://doi.org/10.1021/jacs.5b06823
62. Sujan, A. R.; Kumar, D. R.; Sakwa-Novak, M.; Ping, E. W.; Hu, B.; Park, S. J.; Jones, C. W., Poly(glycidyl amine)-Loaded SBA-15 Sorbents for $CO_2$ Capture from Dilute and Ultradilute Gas Mixtures. *ACS Appl. Polym. Mater.* 2019, 1 (11), 3137-3147. https://doi.org/10.1021/acsapm.9b00788
63. Li, Q.; Mu, X.; Xiao, S.; Wang, C.; Chen, Y.; Yuan, X., Porous aromatic networks with amine linkers for adsorption of hydroxylated aromatic hydrocarbons. *J Appl. Polym. Sci.* 2019, 136 (2), 46919. https://doi.org/10.1002/app.46919
64. Holewinski, A.; Sakwa-Novak, M. A.; Carrillo, J.-M. Y.; Potter, M. E.; Ellebracht, N.; Rother, G.; Sumpter, B. G.; Jones, C. W., Aminopolymer Mobility and Support Interactions in Silica-PEI Composites for CO2 Capture Applications: A Quasielastic Neutron Scattering Study. *J. Phys. Chem. B* 2017, 121 (27), 6721-6731. https://doi.org/10.1021/acs.jpcb.7b04106
65. Carrillo, J.-M. Y.; Potter, M. E.; Sakwa-Novak, M. A.; Pang, S. H.; Jones, C. W.; Sumpter, B. G., Linking Silica Support Morphology to the Dynamics of Aminopolymers in Composites. *Langmuir* 2017, 33 (22), 5412-5422. https://doi.org/10.1021/acs.langmuir.7b00283
66. Serna-Guerrero, R.; Sayari, A., Modeling adsorption of $CO_2$ on amine-functionalized mesoporous silica. 2: Kinetics and breakthrough curves. *Chem. Eng. J* 2010, 161 (1), 182-190. https://doi.org/10.1016/j.cej.2010.04.042
67. Sayari, A.; Belmabkhout, Y., Stabilization of Amine-Containing $CO_2$ Adsorbents: Dramatic Effect of Water Vapor. *J. Am. Chem. Soc.* 2010,132 (18), 6312-6314. https://doi.org/10.1021/ja1013773
68. Heydari-Gorji, A.; Belmabkhout, Y.; Sayari, A., Polyethylenimine-Impregnated Mesoporous Silica: Effect of Amine Loading and Surface Alkyl Chains on $CO_2$ Adsorption. *Langmuir* 2011, 27 (20), 12411-12416. https://doi.org/10.1021/la202972t
69. Sayari, A.; Liu, Q.; Mishra, P., Enhanced Adsorption Efficiency through Materials Design for Direct Air Capture over Supported Polyethylenimine. *ChemSusChem* 2016, 9 (19), 2796-2803. https://doi.org/10.1002/cssc.201600834
70. Didas, S. A.; Zhu, R.; Brunelli, N. A.; Sholl, D. S.; Jones, C. W., Thermal, Oxidative and CO2 Induced Degradation of Primary Amines Used for $CO_2$ Capture: Effect of Alkyl Linker on Stability. *J. Phys. Chem. C* 2014, 118 (23), 12302-12311. https://doi.org/10.1021/jp5025137
71. Chen, C.-H.; Shimon, D.; Lee, J. J.; Mentink-Vigier, F.; Hung, I.; Sievers, C.; Jones, C. W.; Hayes, S. E., The "Missing" Bicarbonate in $CO_2$ Chemisorption Reactions on Solid Amine Sorbents. *J. Am. Chem. Soc.* 2018, 140 (28), 8648-8651. https://doi.org/10.1021/jacs.8b04520
72. Wang, J.; Huang, H.; Wang, M.; Yao, L.; Qiao, W.; Long, D.; Ling, L., Direct Capture of Low-Concentration $CO_2$ on Mesoporous Carbon-Supported Solid Amine Adsorbents at Ambient Temperature. *Ind. Eng. Chem. Res.* 2015, 54 (19), 5319-5327. https://doi.org/10.1021/acs.iecr.5b01060
73. Serna-Guerrero, R.; Da'na, E.; Sayari, A., New Insights into the Interactions of $CO_2$ with Amine-Functionalized Silica. *Ind. Eng. Chem. Res.* 2008, 47 (23), 9406-9412. https://doi.org/10.1021/ie801186g
74. Lee, J. J.; Chen, C.-H.; Shimon, D.; Hayes, S. E.; Sievers, C.; Jones, C. W., Effect of Humidity on the $CO_2$ Adsorption of Tertiary Amine Grafted SBA-15. *J Phys. Chem. C* 2017, 121 (42), 23480-23487. https://doi.org/10.1021/acs.jpcc.7b07930
75. Su, F.; Lu, C.; Chen, H.-S., Adsorption, Desorption, and Thermodynamic Studies of $CO_2$ with High-Amine-Loaded Multiwalled Carbon Nanotubes. *Langmuir* 2011, 27 (13), 8090-8098. https://doi.org/10.1021/la201745y
76. Liu, Q.; Xiong, B.; Shi, J.; Tao, M.; He, Y.; Shi, Y., Enhanced Tolerance to Flue Gas Contaminants on Carbon Dioxide Capture Using Amine-Functionalized Multiwalled Carbon Nanotubes. *Energy & Fuels* 2014, 28 (10), 6494-6501. https://doi.org/10.1021/ef501614m
77. Wurzbacher, J. A.; Gebald, C.; Piatkowski, N.; Steinfeld, A., Concurrent Separation of $CO_2$ and $H_2O$ from Air by a Temperature-Vacuum Swing Adsorption/Desorption Cycle. *Environ. Sci. Technol.* 2012, 46 (16), 9191-9198. https://doi.org/10.1021/es301953k
78. Gebald, C.; Wurzbacher, J. A.; Borgschulte, A.; Zimmermann, T.; Steinfeld, A., Single-Component and Binary $CO_2$ and $H_2O$ Adsorption of Amine-Functionalized Cellulose. *Environ. Sci. Technol.* 2014, 48 (4), 2497-2504. https://doi.org/10.1021/es404430g Additional Material for Example 1

Materials: Pluronic P-123 block copolymer, tetraethyl orthosilicate (TEOS, 99.9%), hydrochloric acid (37%), 1,3,5-tris(bromomethyl)benzene (97%), hexakis(bromomethyl) benzene (98%), ethylenediamine (≥99.5%), propane-1,3-diamine (≥99%), potassium bromide (≥99%), deuterium oxide ($D_2O$, 99.9%) and anhydrous tetrahydrofuran (THF) were purchased from Millipore Sigma Sigma-Aldrich Ltd. and were used as received without any further purifications.

Methanol was obtained from VWR. Ultra-high purity helium and 21% $O_2$/He were obtained from Airgas. Carbon dioxide balanced with helium (400 ppm $CO_2$/He) was obtained from MathesonTri-Gas, Inc.

Syntheses:

Scheme S1. Schematic illustration of the tri-subtituted ethylene diamine benzene (Ph-3-ED) synthesis.[1]

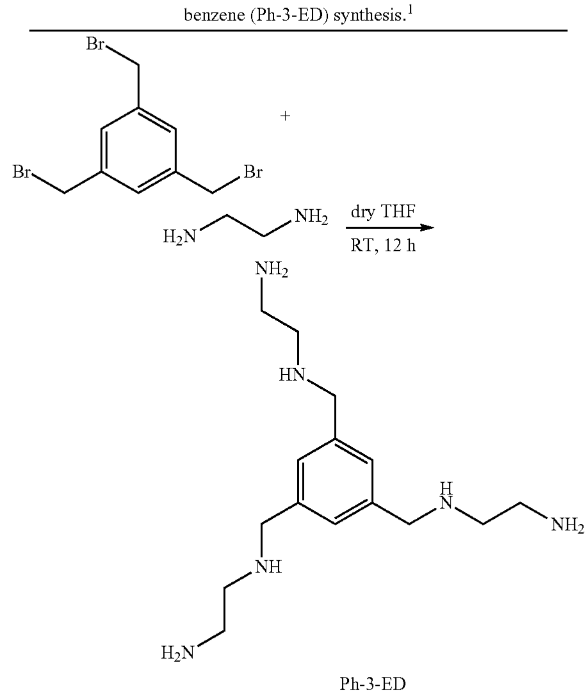

Ph-3-ED

Synthesis of Ph-3-ED. In a 100 mL round bottom flask (RBF), 1,3,5-tris(bromomethyl)benzene (Ph-3-$CH_2$Br) (2 g, 5.6 mmol) was dissolved in dry THF (60 mL) under argon at room temperature. This solution was added dropwise to a 250 mL RBF containing excess ethylenediamine (13.5 g, 224 mmol) at room temperature under argon. After complete addition, the reaction mixture was stirred overnight at room temperature. The solvent and excess ethylenediamine were removed by reduced pressure (rotary evaporation). Subsequently, the resulting brown viscous oil was dissolved in methanol (15 mL). Potassium hydroxide (0.9 g, 16.8 mmol) was added and the mixture was stirred for 1 hour. The inorganic salt (KBr) was precipitated by addition of diethyl ether and removed by gravity filtration. The filtrate was rotary evaporated to afford a highly viscous oil (1.58 g, 96% yield). $^1$H NMR, ($D_2O$, 700 MHz), δ (ppm): 7.21 (3H, s), 3.73 (6H, s), 2.71 (6H, t), 2.61 (6H, t). $^{13}$C NMR, ($D_2O$, 175 MHz), δ (ppm): 139.76, 127.39, 52.14, 50.01, 39.82. m/z: found; $[M+H]^+$ 295.2607, calc. for $[M+H]^+$ 295.2605.

Scheme S2. Schematic illustration of the tri-subtituted propane diamine benzene (Ph-3-PD) synthesis.

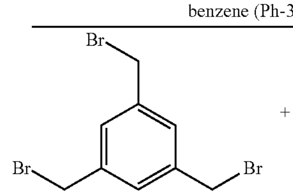

+

-continued

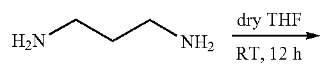

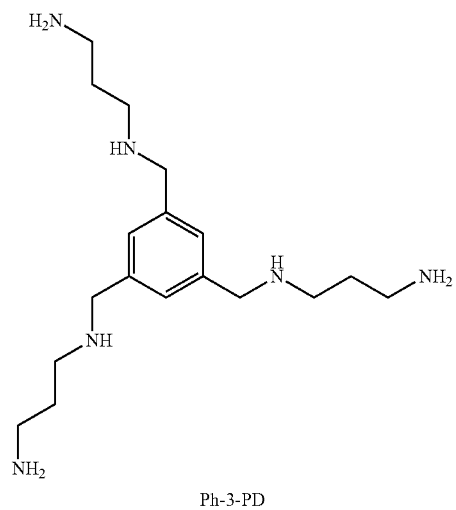

Ph-3-PD

Synthesis of Ph-3-PD: In a 100 mL round bottom flask, 1,3,5-tris(bromomethyl)benzene (Ph-3-$CH_2$Br) (2 g, 5.6 mmol) was dissolved in dry THF (60 mL) under argon at room temperature. This solution was added dropwise to a 250 mL RBF containing excess propane-1,3-diamine (16.6 g, 224 mmol) at room temperature under argon. After complete addition, the reaction mixture was stirred overnight at room temperature. The solvent and excess propane-1,3-diamine were removed under reduced pressure using a rotary evaporator. Subsequently, the resulting colorless viscous oil was dissolved in methanol (15 mL). Potassium hydroxide (0.95 g, 16.8 mmol) was added and the mixture was stirred for 1 hour. The inorganic salt (KBr) was precipitated by addition of diethyl ether and removed by gravity filtration. The filtrate was rotary evaporated to afford a highly viscous oil (1.8 g, 95% yield). $^1$H NMR, ($D_2O$, 700 MHz), δ (ppm): 7.20 (3H, s), 3.72 (6H, s), 2.67 (6H, t), 2.58 (6H, t), 1.65 (6H, q). $^{13}$C NMR, ($D_2O$, 175 MHz), δ (ppm): 139.56, 127.52, 52.17, 45.38, 38.48, 30.48. m/z: found; $[M+H]^+$ 337.3078, calc. for $[M+H]^+$ 337.3074.

Scheme S3. Schematic illustration of the hexa-subtituted ethylene diamine benzene (Ph-6-ED) synthesis.

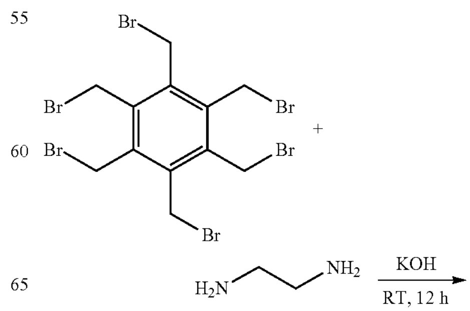

-continued

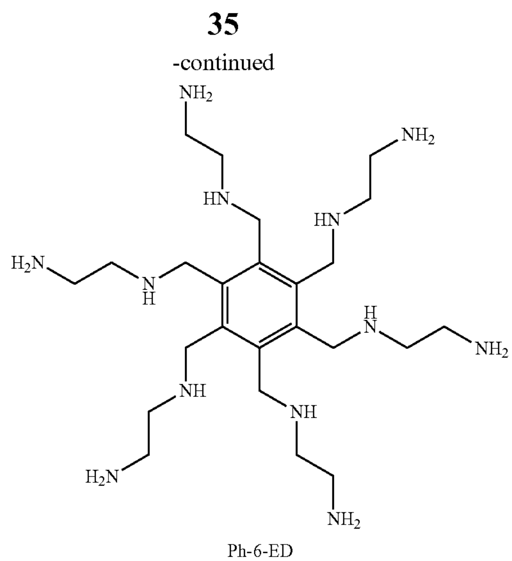

Ph-6-ED

-continued

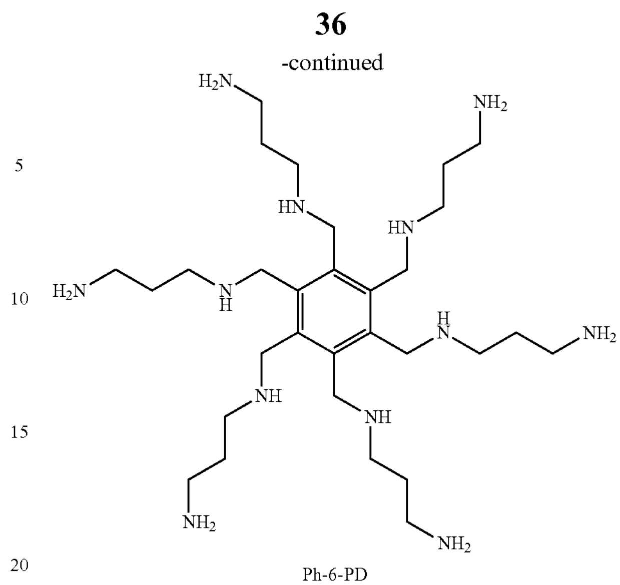

Ph-6-PD

Synthesis of Ph-6-ED: In a 100 mL round bottom flask, 1,2,3,4,5,6-hexakis(bromomethyl)benzene ($Ph-6-CH_2Br$) (1.5 g, 2.36 mmol), excess ethylenediamine (8.5 g, 141.5 mmol) and KOH (0.7 g, 14.2 mmol) were added under argon atmosphere. The reaction mixture was stirred overnight at room temperature. Excess diamine was removed under reduced pressure (rotary evaporation). The resulting brown and viscous product was dissolved in methanol (10 mL). The inorganic salt (KBr) was precipitated by addition of diethyl ether and removed by gravity filtration. The filtrate was rotary evaporated to afford a highly viscous brown oil. The product was dried on a high vacuum line to remove trace amine (0.7 g, 58% yield). $^1H$ NMR, ($D_2O$, 700 MHz), δ (ppm): 3.80 (12H, s), 2.80 (24H, m). $^{13}C$ NMR ($D_2O$, 175 MHz), δ (ppm): 137.46, 51.76, 47.03, 39.79. m/z: Found; $[M+H]^+$ 511.4663, calc. for $[M+H]^+$ 511.4667.

Scheme S4. Schematic illustration of the hexa-subtituted propane diamine benzene (Ph-6-PD) synthesis.

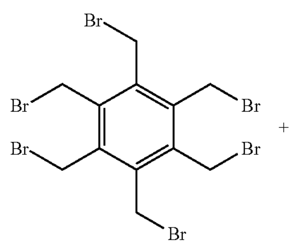

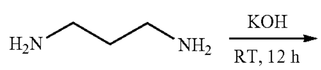

Synthesis of Ph-6-PD: In a 100 mL round bottom flask, 1,2,3,4,5,6-hexakis(bromomethyl)benzene (1.5 g, 2.36 mmol), excess propane-1,3-diamine (10.5 g, 141.59 mmol) and KOH (0.82 g, 14.63 mmol) were added under argon atmosphere. The reaction mixture was stirred overnight at room temperature. Excess propane-1,3-diamine was removed under reduced pressure (rotary evaporation). Subsequently, the resulting colorless viscous product was dissolved in methanol (10 mL). The inorganic salt (KBr) was precipitated by addition of diethyl ether and separated by filtration. The filtrate was evaporated to afford a highly viscous yellow liquid (1.2 g, 85% yield). $^1H$ NMR, ($D_2O$, 700 MHz), δ (ppm): 3.78 (12H, s), 2.77 (12H, t), 2.67 (12H, t), 1.69 (12H, q). $^{13}C$ NMR, ($D_2O$, 175 MHz), δ (ppm): 137.42, 47.22, 46.90, 38.76, 31.38. m/z: found; $[M+H]^+$ 595.5602, calc. for $[M+H]^+$ 595.5606.

Synthesis of mesoporous SBA-15: Mesoporous SBA-15 was prepared following a well-known procedure.[2] The mesoporous SBA-15 used in this study had a surface specific area BET of 700 $m^2/g_{SiO2}$ and total pore volume of 0.96 $cm^3/g_{SiO2}$.

General preparatory procedure for the Ph-X-YY/SBA-15 sorbents: Ph-XX-YY/SBA-15 composites with desired loadings were prepared by the well-established wet impregnation method reported in the literature.[2-6] First SBA-15 was pretreated under vacuum conditions at 110° C. overnight to remove adsorbed moisture and atmospheric $CO_2$. Then for each composite formulation SBA-15 (200 mg) and methanol (50 mL) were mixed into a round bottom flask (100 mL) and stirred for 2 h. Separately, in a scintillation glass vial (20 mL), the desired amount of Ph-X-YY was dissolved in methanol (10 mL) and stirred for 10-15 min. Ph-X-YY solution was added to SBA-15/methanol mixture and stirred overnight at room temperature. The solvent was removed under reduced pressure (rotary evaporation). The resulting powder was dried overnight under vacuum (<20 mTorr) at 50° C. The actual percentage (%) loading was determined by using thermogravimetric analysis (TGA). All prepared composite powders were stored in glass vials at ambient conditions and used for further studies.

The percentage loading of the polymer in the composite was varied by using equation 1.

$$\% \text{ Loading}=\alpha/(\alpha+\beta)\times 100 \quad \text{Equation: 1}$$

where α represents the mass of added Ph-X-YY (g) and f represents the mass of SBA-15 silica support (g).

Methods: Nuclear magnetic resonance (NMR) spectra were obtained on Bruker spectrometers operating at either 400 or 700 MHz, for $^{1}H$ nuclei and 101 or 175 MHz for $^{13}C$ nuclei. Chemical shifts are reported in ppm relative to the indicated residual solvent (4.79 ppm for $D_2O$). Electrospray ionization mass spectroscopy (ESI-MS) analysis was performed on ThermoFisher Scientific LTQ Orbitrap XL ETD is a high performance, hybrid linear ion trap/orbitrap tandem mass spectrometer.

The actual organic loading of the Ph-X-YY/SBA-15 composites was determined thermogravimetrically by using a STA409PG TGA/DSC instrument from Netzsch that simultaneously performs thermogravimetric and differential scanning calorimetry measurements. The organic content was determined from the difference in mass loss between the 120° C.-900° C. temperature interval upon heating in nitrogen-diluted air. The amine loading of samples was determined by elemental analysis (EA) performed at the Atlantic Microlabs LLC, Atlanta, Ga. $N_2$ physisorption measurements were carried out with a Micromeritics Tristar II 3020 instrument. Before the measurement, the samples were kept under vacuum at 110° C. for at least 12 h to remove adsorbed moisture and $CO_2$. The Brunauer-Emmett-Teller (BET) surface area was analyzed in the range of $P/P_0$ from 0.1 to 0.3; the total pore volume was calculated based on the $N_2$ uptake at $P/P_0$ of 0.95, and pore size distributions were calculated by the Brunauer-Emmet-Teller (BJH) method, using the MicroActive software package by Micromeritics.

$CO_2$ adsorption capacities were measured gravimetrically using a Q500 TGA apparatus from TA Instruments. The program used consisted of the following steps: the samples were heated to 110° C. at a ramp rate of 10° C. $min^{-1}$ under the flow of He and held isothermally for 2 h to remove moisture and adsorbed atmospheric $CO_2$. The samples were then cooled to 35° C. at the same rate and equilibrated for 1 h. Subsequently, the gas flow was switched to a premixed gas containing 400 ppm $CO_2$/He and kept isothermally for 12 h. The mass gained during the 12 h was used to calculate the amount of $CO_2$ adsorbed.

Cyclic adsorption/desorption experiments were performed gravimetrically with the same Q500 TGA instrument. After isothermal heating for 2 h at 110° C. the samples were cooled at 35° C. and equilibrated for 2 h. Then the gas was alternatively switched to $CO_2$/He 35° C. and kept for 1 h adsorption followed by switching to He and isothermal heating to 90° C. for 10 min. The latter program sequence enables the desorption of $CO_2$ (sorbent regeneration). The last two sequences, adsorption $CO_2$ at 35° C. and desorption $CO_2$ at 90° C., were repeated 25 times with an equilibration time of 10 min in between.

Accelerated oxidation of the composites was performed gravimetrically using a Q500 TGA instrument from TA Instruments. The Ph-X-YY/SBA-15 composites were treated at either 110° C. or 90° C. under a flow of 21% $O_2$/He (90 mL/min) and held for 24 h. Subsequently, the temperature was ramped to 35° C. and the gas was switched to 400 ppm $CO_2$. The sample was held isothermally for 12 h.

Fix bed experimental procedure: Dry and humid $CO_2$ capacities were determined by using an in-house made glass fritted fixed bed system previously reported by Lee et. al.[7,8] $CO_2$ adsorption was performed using 400 ppm $CO_2$ balanced with He with a constant flow rate of 90 mL/min at 35° C.

It should be noted that ratios, concentrations, amounts, dimensions, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a range of "about 0.10% to about 5%" should be interpreted to include not only the explicitly recited range of about 0.1% to about 5%, but also include individual ranges (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the numerical value and measurement technique. In addition, the phrase "about 'x' to 'y'" includes "about 'x' to about 'y'".

It should be emphasized that the above-described embodiments of this disclosure are merely possible examples of implementations, and are set forth for a clear understanding of the principles of this disclosure. Many variations and modifications may be made to the above-described embodiments of this disclosure without departing substantially from the spirit and principles of this disclosure. All such modifications and variations are intended to be included herein within the scope of this disclosure and protected by the following claims.

Therefore, the following is claimed:

1. A method of separating $CO_2$ from a gas mixture, comprising:

capturing the $CO_2$ from the gas mixture by exposing the gas mixture to an alkyl diamine-substituted aryl compound having one of the following structures:

Ph-3-ED

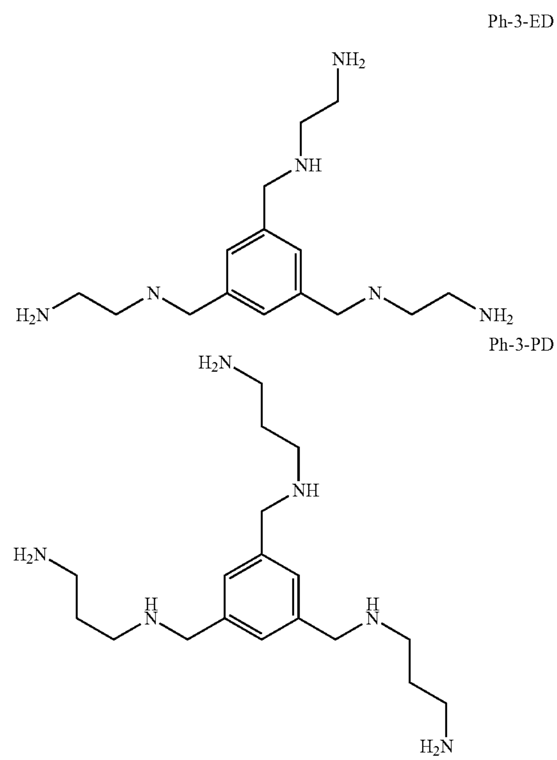

Ph-3-PD

-continued

Ph-6-ED

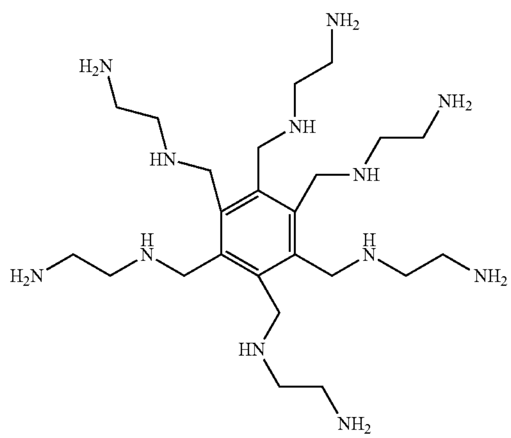

Ph-6-PD

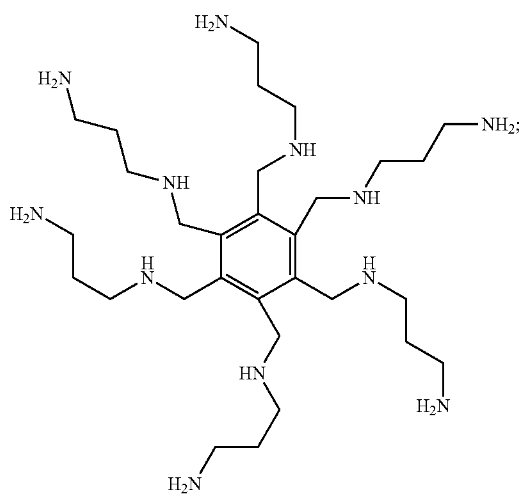

releasing the $CO_2$ from the alkyl diamine-substituted aryl compound and capturing the released $CO_2$ for further storage and/or processing.

2. The method of claim 1, wherein the gas mixture comprises ambient air or a mixture of ambient air and flue gas.

3. The method of claim 1, wherein the alkyl diamine-substituted aryl compound is supported on a porous structure.

4. The method of claim 3, wherein the loading of the alkyl diamine-substituted aryl compound on the porous structure is 20 wt % to 60 wt % versus the combined weight of the alkyl diamine-substituted aryl compound and the porous structure based on thermogravimetric analysis.

5. The method of claim 3, wherein the alkyl diamine-substituted aryl compound is physically impregnated in the porous structure.

6. The method of claim 1, wherein the alkyl diamine-substituted aryl compound is capable of reaching at least 50% saturation within 200 minutes of exposure to 400 ppm $CO_2$/He at 35° C.

7. The method of claim 4, wherein exposing includes flowing the gas mixture across the surface of the porous structure.

8. The method of claim 1, further comprising measuring the amount of captured $CO_2$ that is released from the alkyl diamine-substituted aryl compound.

9. The method of claim 1, wherein releasing the $CO_2$ comprises heating the alkyl diamine-substituted aryl compound to above room temperature.

10. The method of claim 1, wherein the gas mixture comprises flue gas.

11. The method of claim 1 further comprising, after releasing the $CO_2$ from the alkyl diamine-substituted aryl compound, performing a further step of capturing $CO_2$ from the same gas mixture or a second gas mixture by exposing the same or the second gas mixture to the $CO_2$ depleted alkyl diamine-substituted aryl compound.

12. The method of claim 1, further comprising storing the captured $CO_2$.

* * * * *